United States Patent [19]
Hong et al.

[11] Patent Number: 6,165,765
[45] Date of Patent: Dec. 26, 2000

[54] DNA POLYMERASE HAVING ABILITY TO REDUCE INNATE SELECTIVE DISCRIMINATION AGAINST FLUORESCENT DYE-LABELED DIDEOXYNUCLEOTIDES

[75] Inventors: GuoFan Hong, Shanghai; Wei-hua Huang, Zhejiang, both of China

[73] Assignee: Shanghai Institute of Biochemistry, Chinese Academy of Sciences, Shanghai, China

[21] Appl. No.: 09/157,397

[22] Filed: Sep. 21, 1998

Related U.S. Application Data

[63] Continuation-in-part of application No. 08/544,643, Oct. 18, 1995, Pat. No. 5,747,298, and a continuation-in-part of application No. 08/642,684, May 3, 1996, Pat. No. 5,834,253.

[51] Int. Cl.$^7$ .............................. C12N 9/12; C12Q 1/68; C12P 19/34
[52] U.S. Cl. ............................ 435/194; 435/6; 435/91.1; 435/91.2
[58] Field of Search ................................. 435/19 A, 91.1, 435/91.2, 6

[56] References Cited

U.S. PATENT DOCUMENTS

| | | | |
|---|---|---|---|
| 5,614,365 | 3/1997 | Tabor et al. | 435/6 |
| 5,747,298 | 5/1998 | Hong et al. | 435/91.1 |
| 5,834,253 | 11/1998 | Hong et al. | 435/91.1 |

FOREIGN PATENT DOCUMENTS

| | | |
|---|---|---|
| 96/38568 | 12/1996 | WIPO . |
| 98/40496 | 9/1998 | WIPO . |
| 99/10366 | 9/1998 | WIPO . |

OTHER PUBLICATIONS

Joyce, et al., "Function and Structure Relationships in DNA Polymerases", Annu. Rev. Biochem. 1994, vol. 63, pp. 777–822.

Mead et al., "Bst DNA Polymerase Permits Rapid Sequence Analysis from Nanogram Amounts of Template", Research Report, BioTechniques, vol. 11, No. 1 (1991), pp. 76–84.

McClary, et al., "Sequencing with the large fragment . . . stearothermophilus", DNA Sequence–J. DNA Sequencing and Mapping, vol. 1, (1991) pp. 173–180.

Epicentre Technlogies, "What's New in this Catalog?" DNA Polymerase ( . . . fragment), 1994/95 Products for Molecular & Cellular Biology, p. 1.

Jacobsen et al., "The N–Terminal Amino–Acid Sequences of DNA Polymerase I from Escherichia coli and of the Large and the Small Fragments Obtained by a Limited Proteolysis", Eur. J. Biochem. 45 (1974), pp. 623–627.

John Wiley & Sons, Inc., Current Protocols in Molecular Biology, DNA Sequencing, vol. 1, 1994, pp. 7.4.31–7.4.33.

Sanger et al., "DNA sequencing with chain–terminating inhibitors", Biochemistry: Proc. Natl. Acad. Sci. USA 74, No. 12, (1977), pp. 5463–5467.

Shengyu et al., Heat–stable DNA Polymerase I Large Fragment Resolves Hairpin Structure in DNA Sequencing, Scientia Sinica (Series B), vol. XXX, No. 5, May 1987, pp. 503–506.

Okazaki et al., "Enzymatic Synthesis of Deoxyribonucleic Acid", The Journal of Biological Chemistry, vo. 239, No. 1, Jan. 1964, pp. 259–268.

Kaboev, et al., "Purification and Properties of Deoxyribonucleic Acid Polymerase from Bacillus stearothermophilus", Journal of Bacteriology, vol. 145, No. 1, Jan. 1981, pp. 21–26.

Catalogue of Bacteria and Phages, American Type Culture Collection, Eighteenth edition, 1992, p. 51.

Riggs et al., Construction of single amino acid substitution mutants of cloned Bacillus stearothermophilus DNA polymerase I which lacks 5'-3' exonuclease activity, Biochimica et Biophysica Acta 1307 (1996), pp. 178–186.

Aliotta et al., "Thermostable Bst DNA polymerase I lacks a 3'-5' proofreading exonuclease activity", Genetic Analysis Biomolecular Engineering, 12 (1996), pp. 185–195.

Earley, et al., "Robotic Automation of Dideoxyribonucleotide Sequencing Reactions", Research Reports, BioTechniques, vol. 17, No. 1 (1994) 156–165.

Mardis et al., "Automated Methods for Single–Stranded DNA Isolation and Dideoxynucleotide DNA Sequencing Reactions on a Robotic Workstation", Research Report, BioTechniques, vol. 7, No. 8 (1989) pp. 840–850.

BIO RAD, US Bulletin 1649, Pre–mixed Nucleotide Sequencing Kits for Bst® DNA Polymerase, 1996, pp. 176–178.

Carroll et al., "A Mutant of DNA Polymerase I (Klenau Fragment) with reduced Fidelity", Biochemistry, vol. 30, No.3, 1991, pp. 804–813.

BIO RAD, US Bulletin 1771, Fluorescent–labeled DNA Sequencing Reactions Using Bst Polymerase 1996, pp.1–4.

Promega Technical Bulletin, "Sequence of pGEM3z(+) Vector", Revised 2/95, pp. 5–6.

Chissoe, "Strategies for Rapid and Accurate DNA Sequencing", Methods: A Companion to Methods in Enzymology, vol. 3, No. 1, (Aug., 1991) pp. 55–65.

Kunkel, "Rapid and Efficient Site–Specific Mutagenesis without Phenotypic selection", Methods in Enzym., vol. 154 (1987), pp. 367–383.

*Primary Examiner*—Einar Stole
*Attorney, Agent, or Firm*—Nash & Titus, LLC

[57] ABSTRACT

The invention relates to genetical modification of DNA polymerase to reduce its innate selective sequence-related discrimination against incorporation of fluorescent dye-labeled ddCTP and ddATP in the enzymatic reaction for preparation of samples for automated florescent dye-labeled terminator DNA sequencing. The modified DNA polymerases are more resistant to heat inactivation and are more effective in dideoxynucleotide incorporation than current DNA polymerases.

16 Claims, 18 Drawing Sheets

DNA POLYMERASE HAVING ABILITY TO REDUCE INNATE SELECTIVE DISCRIMINATION AGAINST FLUORESCENT DYE-LABELED DIDEOXYNUCLEOTIDES

This application is a continuation-in-part application of Ser. No. 08/544,643 (now U.S. Pat. No. 5,747,298), filed Oct. 18, 1995, and Ser. No. 08/642,684, filed May 3, 1996, now U.S. Pat. No. 5,834,253, and the entire contents of both applications are incorporated herein by reference.

BACKGROUND OF THE INVENTION

The genetic material of all known living organisms is deoxyribonucleic acid (DNA), except in certain viruses whose genetic material may be ribonucleic acid (RNA). DNA consists of a chain of individual deoxynucleotides chemically linked in specific sequences. Each deoxynucleotide contains one of the four nitrogenous bases which may be adenine (A), cytosine (C), guanine (G) or thymine (T), and a deoxyribose, which is a pentose, with a hydroxyl group attached to its 3' position and a phosphate group attached to its 5' position. The contiguous deoxynucleotides that form the DNA chain are connected to each other by a phosphodiester bond linking the 5' position of one pentose ring to the 3' position of the next pentose ring in such a manner that the beginning of the DNA molecule always has a phosphate group attached to the 5' carbon of a deoxyribose. The end of the DNA molecule always has an OH (hydroxyl) group on the 3' carbon of a deoxyribose.

DNA usually exists as a double-stranded molecule in which two antiparallel DNA strands are held together by hydrogen bonds between the bases of the individual nucleotides of the two DNA strands in a strictly matched "A—T" and "C—G" pairing manner. It is the order or sequence of the bases in a strand of DNA that determines a gene which in turn determines the type of protein to be synthesized. Therefore, the accurate determination of the sequence of the bases in a DNA strand which also constitutes the genetic code for a protein is of fundamental importance in understanding the characteristics of the protein concerned.

The process used to determine the sequence of the bases in a DNA molecule is referred to as DNA sequencing. Among the techniques of DNA sequencing, the enzymatic method developed by Sanger et al. (1) is most popular. It is based on the ability of a DNA polymerase to extend a primer annealed to the DNA template to be sequenced in the presence of four normal deoxynucleotide triphosphates (dNTPs), namely, DATP, dCTP, dGTP and dTTP, and on the ability of the nucleotide analogs, the dideoxynucleotide triphosphates (ddNTPs), namely, ddATP, ddCTP, ddGTP and ddTTP, to terminate the extension of the elongating deoxynucleotide polymers at various lengths.

In the classic one-step Sanger method, the sequence determination is carried out in a set of four separate tubes, each containing all four normal dNTPs, one of which is labeled with a radioactive isotope, $^{32}$P or $^{35}$S, for autoradiographic localization, a limiting amount of one of the four ddNTPs, a DNA polymerase, a primer, and the DNA template to be sequenced. As a result of the DNA polymerase activity, individual nucleotides or nucleotide analogs are added to the new DNA chains, all starting from the 3' end of the primer in a 5'-3' direction, and each linked to adjacent ones with a phosphodiester bond in a base sequence complementary to the DNA sequence of the template. Inasmuch as there is a nucleotide analog in the reaction mixture, each tube eventually contains numerous newly formed DNA strands of various lengths, all ending in a particular ddNTP, referred to as A, C, G or T terminator.

After resolving the four sets of reaction products by high-resolution polyacrylamide/urea gel electrophoresis, the populations of the newly formed DNA strands are separated and grouped according to their molecular weight. An autoradiographic image of the gel will show the relative positions of these DNA strands as bands which differ from one another in distance measured by one nucleotide in length, all sharing an identical primer and terminating with a particular ddNTP (A, C, G or T). By reading the relative positions of these bands in the "ladder" of the autoradiograph, the DNA sequence of the template can be deduced.

The DNA polymerase used in the reaction mixture plays a pivotal role in DNA sequencing analysis. To be useful for DNA sequencing, a DNA polymerase must possess certain essential properties. For example, it must have its natural 5'-3' exonuclease activity removed by mutagenesis or by posttranslational modification, such as enzymatic digestion, and must be able to incorporate dNTPs and ddNTPs, without undue discrimination against ddNTP and with a sufficiently high processivity which refers to the ability of the enzyme to polymerize nucleotides onto a DNA chain continuously without being dislodged from the chain, and a sufficiently high elongation rate. A 5'-3' exonuclease activity associated with a DNA polymerase will remove nucleotides from the primer, thus cause a heterogeneous 5' end for the newly formed DNA strands, resulting in a false reading of the strand lengths on the sequencing gel. A DNA polymerase with a low processivity and a low elongation rate will cause many undesirable noise background bands of radioactivity due to the presence of DNA strands which are formed with improper lengths and improper terminations. Among the more commonly used DNA polymerases, Sequenase™ has a higher processivity and a higher elongation rate than others, such as the Klenow fragment, Taq, and Vent polymerases (2), and is therefore one of the most popular DNA polymerase selected for DNA sequencing to-date.

However, even when a DNA polymerase has been endowed with all the essential properties listed above, it may still generate erroneous or misleading band patterns of radioactivity in the sequencing gel. These artifactual patterns do not faithfully reflect the true nucleotide sequence in the template being sequenced. They may be caused by premature termination of the elongating strands due to the presence of secondary structures formed along the template, such as "hairpins" in the regions that contain palindromic sequences or that are rich in G and C bases (3); or, they may occur as a result of inadequate "proof-reading" function of the DNA polymerase that will allow the removal of misincorporated nucleotides at the 3' end of an elongating strand.

Researchers in the field of DNA sequencing often have to use several approaches to confirm their findings in order to avoid being misled by these potentially erroneous sequence data. For example, they sometimes rely on repeating the same sequencing experiment with different DNA polymerases, or performing another sequencing reaction with the template which is complementary to the first single-stranded DNA template, and compare the results for possible discrepancies.

Numerous investigators have tried to find an ideal DNA polymerase for enzymatic sequencing, i.e. an enzyme that not only has all the essential properties required for sequencing reaction, but also is capable of resolving the secondary hairpin structures and preventing the formation of strands containing nucleotides non-complementary to those of the template being sequenced.

The discovery by Ye and Hong (4) of the thermostable large fragment of DNA polymerase isolated from Bacillus stearothermophilus (Bst), an enzyme that is functional over the temperature range between 25° C. and 75° C., but is most active at 65° C., and possesses all the essential properties for DNA sequencing, has largely solved the problem caused by secondary structures in the template since these secondary structures are destabilized when the sequencing reaction is carried out at 65° C. In the past few years since this enzyme was made commercially available under the name of Bst DNA Polymerase (Bio-Rad Laboratories), independent reports have confirmed that during sequencing reaction catalyzed by this enzyme all four dNTPs, including dCTP, and other nucleotide analogs, such as dITP and 7-deaza-dGTP, are incorporated equally effectively in the chain elongation, thus eliminating the weak "C" band phenomena often observed when other DNA polymerases are used, and producing a very good band uniformity on the sequencing gel. It has been further established that at this elevated temperature Bst DNA polymerase system can be used both for the classic Sanger one-step reaction as well as for the "labeling/termination" sequencing reaction, double-stranded DNA sequencing, and the incorporation of $^{35}$S-labeled nucleotides, and $^{32}$P-labeled nucleotides. Since this system can be placed at room temperature for at least two weeks without significant loss of its enzymatic activity, it has been adapted for automation of DNA sequencing which requires a stable DNA polymerase, using either fluorescent dye or radioactive isotope labeling. (See also 9, 12, and 13.)

However, when this Bst enzyme is used for automated fluorescent DNA sequencing, only partially satisfactory results have been obtained with fluorescent dye-labeled primers (see 12 and EG Bulletin 1771 of Bio-Rad Laboratories), and even less satisfactory results are obtained with fluorescent dye-labeled ddNTP terminators. Even when fluorescent dye-labeled primers are used, a significant number of mismatched ddNTPs are incorporated onto the 3' end of the extending nucleotides in the enzymatic reaction, thus generating erroneous sequencing data (see Bio-Rad EG Bulletin 1771). With this in mind, the inventors sought, and found, a better DNA polymerase for DNA sequencing, especially for automated fluorescent dye-labeled primer and fluorescent dye-labeled terminator sequencing.

Another disadvantage of the Bst DNA polymerase currently known in the art is its lack of 3'-5' exonuclease activity (5), and specifically, proof-reading 3'-5' exonuclease activity. A survey of the sequencing data collected from fourteen research centers which have used this Bst DNA polymerase for their DNA sequencing work on over 120 DNA clones showed that, statistically, base pair mismatching occurs at a rate of about $1.5 \times 10^{-5}$. That is, approximately 1.5 errors can be expected in one hundred thousand nucleotide incorporations during nucleotide polymerization catalyzed by the enzyme.

It is generally known that the formation of incorrect DNA sequences due to mismatching of base pairs between the template and the growing nucleotide chain in DNA sequencing may be prevented by a 3'-5' exonuclease activity which "proof-reads" the nucleotide chain. However, even if a DNA polymerase exhibits 3'-5' exonuclease activity in vitro, it is often the case that the polymerase will not adequately "proof-read". Thus, the polymerase will not be capable of removing mismatched nucleotides from a newly formed DNA strand as efficiently as those nucleotides correctly matched with the nucleotides of the template. In other words, a 3'-5' exonuclease may excise the correctly matched nucleotides at a faster rate than the mismatched ones from the 3' terminus, or excise both the correctly matched and the mismatched nucleotides at the same rate. Consequently, even where the DNA polymerase has 3'-5' exonuclease activity, it does not perform any useful proof-reading function during DNA polymerization.

It is also known that a 3'-5' exonuclease activity associated with a DNA polymerase, in the presence of low concentrations of dNTPs, often counteracts the normal chain elongation process catalyzed by the polymerase, induces cyclic incorporation and degradation of nucleotides over the same segment of template, or even operates more efficiently than the polymerase activity per se, to the extent of causing degradation of the primer. Consequently, removal of the 3'-5' exonuclease activity along with the 5'-3' exonuclease activity from the native DNA polymerases by chemical means or by genetic engineering techniques has become a standard procedure in producing DNA polymerases for sequencing. This is a common strategy to preserve the essential properties of a DNA polymerase.

For example, among the major commercially available sequencing enzymes (other than the native Taq (*Thermus aquaticus*) DNA polymerase which lacks a 3'-5' exonuclease activity de novo) the 3'-5' exonuclease activity has been removed from the native T7 DNA polymerase, which lacks a 5'-3' exonuclease, either by a chemical reaction that oxidizes the amino acid residues essential for the exonuclease activity (Sequenase™ Version 1) or genetically by deleting 28 amino acids essential for the 3'-5' exonuclease activity (Sequenase™ 2).

Vent$_R$(exo$^-$) DNA polymerase, which is recommended as the preferred form of the Vent DNA polymerase for sequencing, also has its 3'-5' exonuclease activity removed by genetic modification. The native Vent DNA polymerase and the Klenow fragment isolated from the native *E. coli* DNA polymerase I possess a 3'-5' exonuclease; but these enzymes are no longer considered the enzymes of choice for DNA sequencing.

The currently known Bst DNA polymerase (e.g., produced by Bio-Rad Laboratories) isolated and purified from the cells of *Bacillus stearothermophilus* for DNA sequencing is free of 3'-5' exonuclease activity (5).

IsoTherm™ DNA Polymerase, a commercially available Bst DNA polymerase for DNA sequencing, marketed by Epicentre Technologies (1402 Emil Street, Madison, Wis. 53713), is also based on a Bst DNA polymerase whose 3'-5' exonuclease activity has been enzymatically removed (6).

Only the rBst DNA Polymerase produced from an over-expressing recombinant clone in *E. coli*, which is the product of the DNA pol I gene of *Bacillus stearothermophilus*, possesses a 3'-5' exonuclease activity in addition to a 5'-3' exonuclease activity. However, due to the existence of an undesirable 5'-3' exonuclease activity and a 3'-5' exonuclease activity of unknown characteristics, the latter product is not recommended by the company for DNA sequencing (6).

Over the past 10 years there has been a trend to develop and improve the automated fluorescent DNA sequencing technology to replace the classic radioactive isotope labeling manual method for DNA sequencing because of the potential harmful effects of the radioactive materials to humans and because of the need for automated high throughput DNA sequencing systems. In using fluorescent dyes as markers for labeling the DNA strands generated in enzymatic reactions for sequencing, the dyes can be either coupled with the primer, or coupled with the ddNTP terminators, namely the dye-labeled ddATP, dye-labeled ddCTP, dye-labeled ddGTP and dye-labeled ddTTP. Sequencing techniques based on these two forms of labeling of the final enzymatic reaction products are commonly referred to as "dye primer sequencing" and "dye terminator sequencing", respectively.

In the dye primer sequencing, ddNTPs are employed as the chain terminators, as in the original classic Sanger method which uses radioactive isotope as the marker. The molecular structure of ddNTPs are almost identical to that of dNTPs, the natural building blocks of all DNA molecules. Therefore, any DNA polymerase which has been used for radioactive isotope manual DNA sequencing can be easily adapted for fluorescent dye primer DNA sequencing with equally satisfactory results. The disadvantage in the dye primer technology is that the primer for each template to be sequenced must be labeled with four different fluorescent dyes and that the enzymatic reaction must be performed in four separate test tubes each containing only one of the ddNTPs, namely ddATP, ddCTP, ddGTP or ddTTP, as in the classic Sanger radioisotope method.

In the dye terminator technology for DNA sequencing, the fluorescent dye-labeled ddATP, dye-labeled ddCTP, dye-labeled ddGTP and dye-labeled ddTTP are coupled with different fluorescent dyes, each emitting a specific light spectrum, thus directly reporting the type of ddNTP at the 3' terminus of the DNA fragment. Unlike the situations in the dye primer technology in which four different fluorescent dyes are coupled to a primer incorporated into all newly formed DNA strands, these dye-labeled ddNTPs serve the dual function of a specific base terminator and a "color marker". There is no need to label the primer for each new template, and the polymerase DNA extension reaction can be performed in a single test tube to generate the required specifically terminated and specifically dye-labeled DNA fragments of various sizes for DNA sequencing.

The advantage of using fluorescent dye-labeled terminators for DNA sequencing is obvious. However, there are certain difficulties to overcome before an enzymatic reaction system suitable for a radioisotope technique or suitable for a dye primer technique can be adapted for a dye terminator technology. An increase of the molecular weight from less than 500 for a ddNTP terminator to about 800 or more for a fluorescent dye-labeled ddNTP terminator may be associated with potential three-dimensional structural changes. These molecular alterations may interfere with the process of incorporation of the dye-labeled ddNTPs as chain terminators by the DNA polymerase to the 3' end of an extending DNA strand in terms of lowering the rate of incorporation, lowering the processivity of the enzyme for this new substrate, reducing the enzyme-terminator binding specificity and changing the enzyme-terminator binding kinetics.

For example, both Taq DNA polymerase and Sequenase II™ (a T7 DNA polymerase) have been used for radioisotope labeling DNA sequencing with excellent results, and have been adapted for fluorescent dye-labeled primer DNA sequencing. But neither can be used for fluorescent dye-labeled terminator DNA sequencing technologies. As reported in U.S. Pat. No. 5,614,365, when the Taq DNA polymerase was used for fluorescent dye-labeled terminator chemical reactions, the reaction products generated no readable data on the DNA sequencer. Most of the fluorescence was either in unincorporated dye-ddNTPs at the leading front of the test gel, or in fragments greater than several hundred bases in length. Using a Taq DNA polymerase mutant in which the amino acid, phenylalanine, at position 667 of its amino acid sequence has been replaced by a tyrosine and which has an increased ability to incorporate dideoxynucleotides (6,000 times more efficient), to replace the unmodified Taq DNA polymerase for the experiment, the results are significantly improved. This F667Y mutant of Taq DNA polymerase is now marketed by Amersham Life Science, Inc. under the trademark ThermoSequenase™. It is used for cycle-sequencing in which the enzymatic reaction mixture is subjected to numerous cycles of extension-termination, denaturing and annealing to ensure that sufficient dye-terminator-labeled enzymatic reaction products are generated for the DNA sequencing procedure. Because of the low processivity of the parent Taq DNA polymerase, ThermoSequenase™ is not recommended for direct DNA sequencing without precyclings. Like Taq DNA polymerase, ThermoSequenase T lacks a proof-reading exonuclease activity.

*Bacillus stearothermophilus, Bacillus caldotenax* and *Bacillus caldolyticus* are classified as mesophilic microbes; although their DNA polymerases are referred to as thermo-stable (most active at 65° C.) they are inactivated at 70° C. or above. This is contrasted with other enzymes, such as Taq, which are truly thermophilic—that is, their DNA polymerases tolerate and remain active at temperatures higher than 95° C. These mesophilic bacillus strains, especially *Bacillus stearothermophilus*, produce DNA polymerases that are useful in DNA sequencing applications. However, a disadvantage of the DNA polymerases of these strains is that during DNA sequencing they all exhibit a high degree of selective discrimination against incorporation of certain particular members of fluorescent dye-labeled ddNTPs, namely the fluorescent dye-labeled ddCTP and fluorescent dye-labeled ddATP, as terminators onto the 3' end of the extending DNA fragments during enzymatic reaction. This peculiar characteristic of selective discrimination against incorporation of fluorescent dye-labeled ddCTP and ddATP of the natural DNA polymerases isolated from *Bacillus stearothermophilus* and *Bacillus caldotenax* was not previously recognized. Such selective discrimination is apparently sequence-related, and cannot be corrected or compensated by mere adjustment of the concentrations of the dNTPs.

Thus, there is a need for a mesophilic bacillus DNA polymerase that does not selectively discriminate against incorporation of fluorescent dye-labeled ddCTP and ddATP, during dye terminator DNA sequencing.

SUMMARY OF THE INVENTION

This invention addresses the above-described problems associated with mesophilic bacillus DNA polymerases by providing novel DNA polymerases which, during direct DNA sequencing, reduce the innate selective discrimination against the incorporation of fluorescent dye-labeled ddCTP and fluorescent dye-labeled ddATP, without increasing the rate of incorporation of the other two dye-labeled ddNTP terminators (ddTTP and ddGTP) excessively. In particular, this invention provides a novel genetic modification of the amino acid sequence of a highly processive DNA polymerase (such as isolated from *Bacillus stearothermophilus, Bacillus caldotenax* or *Bacillus caldolyticus*) that, unmodified, selectively discriminates against incorporation of fluorescent dye-labeled dideoxynucleotide terminators ddATP and ddCTP (but does not discriminate against incorporation of fluorescent dye-labeled dideoxynucleotide terminators ddTTP and ddGTP). The modification results in a reduction of the innate selective discrimination against incorporation of fluorescent dye-labeled dideoxynucleotide terminators ddATP and ddCTP, such that all four of the ddNTP terminators are effectively incorporated into the DNA primer elongated by the DNA polymerase. Thus, the modified DNA polymerase of this invention is effective in reducing the innate selective discrimination against incorporation of fluorescent dye-labeled dideoxynucleotide terminators ddATP and ddCTP characteristic of the DNA polymerase in its unmodified state.

In particular, the preferred DNA polymerase is a modification of a DNA polymerase isolated from a strain of a mesophilic bacterium, such as *Bacillus stearothermophilus*, *Bacillus caldotenax* or *Bacillus caldolyticus*. The approach of modifying the DNA polymerase described herein may be used to modify other DNA polymerases which share a close amino acid homology of a DNA polymerase isolated from a strain *Bacillus stearothermophilus, Bacillus caldotenax* or *Bacillus caldolyticus*, as long as the unmodified DNA polymerases have a selective discrimination against incorporation of fluorescent dye-labeled dideoxynucleotide ddCTP and/or ddATP as terminators in the enzymatic reaction for preparing materials for automated fluroescent DNA sequencing. Consequently, it is preferred that the modified DNA polymerase has an amino acid sequence that shares not less than 95% homology of a DNA polymerase isolated from a strain of *Bacillus stearothermophilus, Bacillus caldotenax* or *Bacillus caldolyticus*.

The particularly preferred mesophilic species is *Bacillus stearothermophilus*, which is highly heterogeneous. This is indicated by the wide range of DNA base compositions as well as the range of the phenotypic properties of strains assigned to this species (see Bergey's Manual of Systemic Bacteriology, Eds. P.H.A. Sneath, N. S. Mair, M. E. Sharpe and J. G. Holt, Williams & Wilkins, 1986, Vol. 2, page 1135). Therefore, it is reasonable to assume that the amino acid sequences of DNA polymerases isolated from various strains would be heterogeneous with potential functional differences. Although DNA polymerases isolated from the known standard strains of *Bacillus stearothermophilus* have been shown to lack a 3'-5' exonuclease activity, a questionable trace of "contaminating" 3'-5' exonuclease has been observed in a purified DNA polymerase preparations (see Kaboev et al., J. Bacteriology, Vol. 145, page 21–26, 1981).

Consequently, the inventors began to address the above-identified problems in the art by discovering a strain of *Bacillus stearothermophilus* (designated strain No. 320 for identification purposes; described in U.S. Pat. No. 5,747,298) that produces a DNA polymerase (designated Bst 320) with a proof-reading 3'-5' exonuclease activity which is absent in DNA polymerases isolated from other strains of *Bacillus stearothermophilus*. (For this invention, the term "proof-reading" is intended to denote that the DNA polymerase is capable of removing mismatched nucleotides from the 3' terminus of a newly formed DNA strand at a faster rate than the rate at which nucleotides correctly matched with the nucleotides of the template are removed during DNA sequencing.) The strain Bst 320 was deposited on Oct. 30, 1995 in the American Type Culture Collection, located at 12301 Parklawn Drive, Rockville, Md. 20852, and has been given ATCC Designation No. 55719. The DNA polymerase isolated from Bst 320 is composed of 587 amino acids as are the DNA polymerases of other known strains of *Bacillus stearothermophilus*, such as, for instance, the strains deposited by Riggs et al (Genbank Accession No. L42111) and by Phang et al. (Genbank Accession No. U23149). However, the Bst 320 shares only 89.1% sequence identity at protein level with the *Bacillus stearothermophilus* DNA polymerase deposited by Riggs et al., and shares only 87.4% sequence identity at protein level with the *Bacillus stearothermophilus* DNA polymerase deposited by Phang et al. For comparison, the above-referenced enzyme deposited by Riggs et al. and the enzyme deposited by Phang et al. share 96.9% of their amino acid sequence identity.

The inventors studied a thermostable DNA polymerase isolated from a different species, *Bacillus caldotenax* (Bca), which also has an optimum active temperature at 65° C. The inventors discovered that the Bst 320 DNA polymerase shares 88.4% of the amino acid sequence identity with Bca DNA polymerase (Uemori et al. J. Biochem. 113: 401–410, 1993). Based on homology of the amino acid sequences, Bst 320 DNA polymerase is as close to DNA polymerases isolated from *Bacillus stearothermophilus* as to the DNA polymerase isolated from *Bacillus caldotenax*, i.e. another species of bacillus. It was also discovered that both Bst 320 DNA polymerase and Bca DNA polymerase functionally exhibit 3'-5' exonuclease activity, which is not associated with known amino acid sequence exonuclease motifs I, II and III as in the *E. coli* DNA polymerase I model, or other known *Bacillus stearothermophilus* polymerases.

The inventors has studied the DNA polymerases of three different strains of *Bacillus stearothermophilus* (including DNA polymerase obtained from Bst 320) and the DNA polymerase of *Bacillus caldotenax* and found that they all exhibit a high degree of selective discrimination against incorporation of certain particular members of fluorescent dye-labeled ddNTPs, namely the fluorescent dye-labeled ddCTP and fluorescent dye-labeled ddATP, as terminators onto the 3' end of the extending DNA fragments during enzymatic reaction. This is especially the case when the preceding 3' end base of the extending DNA fragment is a dGMP (G) or a dAMP (A). (By "DNTP" it is intended to denote the four commonly known deoxynucleotide triphosphates, DATP, dTTP, dCTP, and dGTP.)

This selective discrimination causes missing peaks and ambiguous peaks on a color plot generated by the automated fluorescent DNA sequencer, and causes loss of sequencing data and erroneous base callings. This is shown in FIGS. 6 and 8.

This disadvantage of the natural bacillus DNA polymerases in fluorescent dye-labeled terminator DNA sequencing cannot be corrected or compensated by mere adjustment of the concentrations of the dNTPs and the fluorescent dye-labeled ddNTPs in the reaction mixture. This selective discrimination against the specific dye-labeled ddNTPs is also sequence-related as demonstrated with respect to Bst in FIGS. 6 and 8, in which the missing or ambiguous "C" peaks and "A" peaks tend to occur immediately following a preceding "G" peak or a preceding "A" peak. Of particular interest is the fact that the "C" and "A" peaks immediately following a preceding "C" or a preceding "T" peak are quite strong and resolvable in the same color plot analysis, indicating that the concentrations of dNTPs and the fluorescent dye-labeled ddCTP and the fluorescent dye-labeled ddATP were adequate for the termination reaction.

According to the structural model studies carried out on *E. coli* DNA polymerase I (Klenow fragment), certain amino acids in a particular region or regions of a DNA polymerase appear to play important roles in dNTP and ddNTP bindings and their final incorporation, and affect discrimination between deoxy and dideoxynucleotide substrates. For example, mutation of the amino acids arginine, asparagine, lysine, tyrosine, phenylalanine, aspartate, and glutamate in certain locations of amino acid sequences of Klenow fragment may affect the binding of dNTP and discrimination between deoxy and dideoxynucleotides. (See: Joyce, C. M., Current Opinion in Structural Biology, 1:123–129, 1991. Joyce and Steitz, Annu. Rev. Biochem., 63:777–822, 1993, page 800. Carrol et al., Biochemistry 30:804–813, 1991).

The problem which faced the inventors was how to reduce the selective discrimination against the incorporation of fluorescent dye-labeled ddCTP and fluorescent dye-labeled ddATP by site-directed mutagenesis of a DNA polymerase, without increasing the rate of incorporation of the other two dye-labeled ddNTP terminators excessively. In particular, the new mutant must be able to incorporate more correctly base-matched dye-labeled ddCTP and/or dye-labeled ddATP terminators to the dGMP (G) and DAMP (A) bases, than to the dCMP (C) and dTMP (T) bases of the extending DNA fragments during enzymatic reaction. A blanket increase in the ability of an enzyme to incorporate all four dye-labeled ddNTPs to the same proportion would serve no useful purpose for the group of DNA polymerases isolated from mesophilic bacilli since, unlike the Taq DNA polymerase, the unmodified natural enzymes of *Bacillus stearothermophilus* and *Bacillus caldotenax* already possess a high ability to incorporate fluorescent dye-labeled ddGTP and fluorescent dye-labeled ddTTP, and even the fluorescent dye-labeled ddCTP and dye-labeled ddATP provided at the immediately preceding base at the 3'end of the extending DNA fragment is not a "G" or an "A".

The inventors found that DNA polymerases isolated from strains of *Bacillus stearothermophilus* and *Bacillus caldotenax* possess the same amino acids at certain specific positions in their amino acid sequence. For example, they all have leucine-glutamate-glutamate at positions corresponding to positions 342–344 and phenylalanine at a position corresponding to position 422 of the amino acid sequence of the DNA polymerase isolated from No 320 strain of *Bacillus stearothermophilus*. The inventors further discovered that the most optimal modification to solve the problem of selective discrimination in direct fluorescent DNA sequencing for these DNA polymerases is to modify the four amino acids of the natural DNA polymerases referenced above in such a form that threonine-proline-leucine substitute respectively for leucine-glutamate-glutamate at positions 342–344 and tyrosine substitutes for phenylalanine at position 422 in their amino acid sequences. Accordingly, the nucleotide sequence encoding the natural forms of the DNA polymerases are modified at positions 1024–1032 from CTC-GAAGAG to ACCCCACTG and at position 1265 from T to A to encode for the DNA polymerases having the desired properties. The combined effects of these amino acid modifications reduce the selective discrimination against incorporation of fluorescent dye-labeled ddCTP and dye-labeled ddATP of the naturally-occurring mesophilic bacillus DNA polymerases during enzymatic reaction for direct automated fluorescent DNA sequencing.

Initially, the DNA polymerases used in the inventors' research were obtained by overexpression of the genes encoding the naturally-occurring enzymes of *Bacillus stearothermophilus* and *Bacillus caldotenax*. Subsequently, modified DNA polymerases obtained by overexpression of the site-directed mutated genes were used. This invention provides both the nucleotide and amino acid sequence for a modified DNA polymerase to illustrate the practice of this new approach of modifying a special group of DNA polymerases, as described below.

In one preferred embodiment, the Bst 320 DNA polymerase is used for the unmodified, naturally-occurring DNA polymerase, although DNA polymerases isolated from other strains of mesophilic bacilli (for instance, *Bacillus stearothermophilus* and *Bacillus caldotenax*) can be used as the starting enzymes for the genetic modification. As noted above, the Bst 320 DNA polymerase is also capable of proofreading 3'-5' exonuclease activity. In particular, the invention provides the DNA and amino acid sequences for the isolated and purified DNA polymerase having this function. These sequences are also described below.

The invention also contemplates an isolated strain of *Bacillus stearothermophilus* which produces a DNA polymerase having an ability to reduce selective discrimination against incorporation of fluorescent dye-labeled dideoxynucleotide terminators ddCTP and ddATP, but not fluorescent dye-labeled dideoxynucleotide terminators ddGTP and ddTTP, in the presence of dNTPs and the four fluorescent dye-labeled dideoxynucleotide terminators. Preferably, the Bst strain produces a DNA polymerase which also has proofreading 3'-5' exonuclease activity during DNA sequencing of a DNA strand from a template.

As mentioned above, the invention also contemplates DNA polymerases obtained or otherwise derived from any bacillus strain, or made synthetically, as long as the amino acid sequences of the naturally-occurring DNA polymerases have leucine-glutamate-glutamate at positions corresponding respectively to positions 342–344 of Bst 320 DNA polymerase and phenylalanine at a position corresponding to position 422 of Bst 320 DNA polymerase. For example, DNA polymerases derived from other strains of *Bacillus stearothermophilus* or *Bacillus caldotenax* or other mesophilic bacilli may be easily modified using conventional DNA modification techniques to include the amino acid or nucleotide substitutions identified above.

The invention also provides a DNA construct comprising at least one of the above-described DNA polymerase sequences and a vector (such as a cloning vector or an expression vector), for introducing the DNA construct into eucaryotic or procaryotic host cells (such as an *E. coli* host cell). In addition, the invention further provides a host cell stably transformed with the DNA construct in a manner allowing production of the peptide encoded by the DNA segment in the construct.

The invention also provides improved methods for replicating DNA and sequencing DNA using the above-described DNA polymerases of the invention. The DNA polymerases are useful in both direct dye terminator DNA sequencing and dye-primer DNA sequencing.

Preferably, the method of sequencing a DNA strand may comprise the steps of:

i) hybridizing a primer to a DNA template to be sequenced;

ii) extending the primer using a DNA polymerase which has an ability to reduce selective discrimination against incorporation of fluorescent dye-labeled dideoxynucleotide terminators ddCTP and ddATP, in the presence of adequate amounts of nucleotide bases DATP, dGTP, dCTP and dTTP, or their analogs, and the four fluorescent dye-labeled dideoxynucleotide terminators, under such conditions that the DNA strand is sequenced.

Further objects and advantages of the invention will become apparent from the description and examples below.

BRIEF DESCRIPTION OF THE DRAWINGS

In the Figures and throughout this disclosure, "HiFi Bst" or "Bst 320" DNA polymerase refers to the unmodified naturally occurring DNA polymerase having proofreading 3'-5' exonuclease activity, either isolated from the cells of No. 320 strain of *Bacillus stearothermophilus* or produced by overexpression of the gene encoding this naturally occurring DNA polymerase. (This Bst strain and DNA polymerase are described in U.S. Pat. No. 5,747,298.) "HiFi Bst-II" refers to the modified form of "HiFi Bst" DNA polymerase which has an ability to reduce selective discrimination against fluorescent dye-labeled ddCTP and ddATP. HiFi Bst-II is an example of one preferred embodiment of this invention.

Y: relative polymerase activity (%)

X: incubation time (minutes).

Figure 2:

FIG. 2. This shows a autoradiograph of a DNA sequencing gel obtained by using radiolabeled primer with HiFi Bst-II and HiFi Bst, and shows the dideoxy-nucleotide incorporation of HiFi Bst-II and HiFi Bst in a reaction mixture with a suboptimally low ddNTP/dNTP ratios.

Template: single-stranded M13mp18;

Primer: −20M13 forward primer.

Figure 3:

FIG. 3. This shows a autoradiograph of a DNA sequencing gel obtained by using radiolabeled DATP with HiFi Bst and HiFi Bst-II in reaction mixtures with optimized ddNTP/dNTP ratios. The sequence pattern with HiFi Bst-II is better than that with HiFi Bst.

Template: single-stranded M13mp18;

Primer: −20M13 forward primer.

Figure 4A:
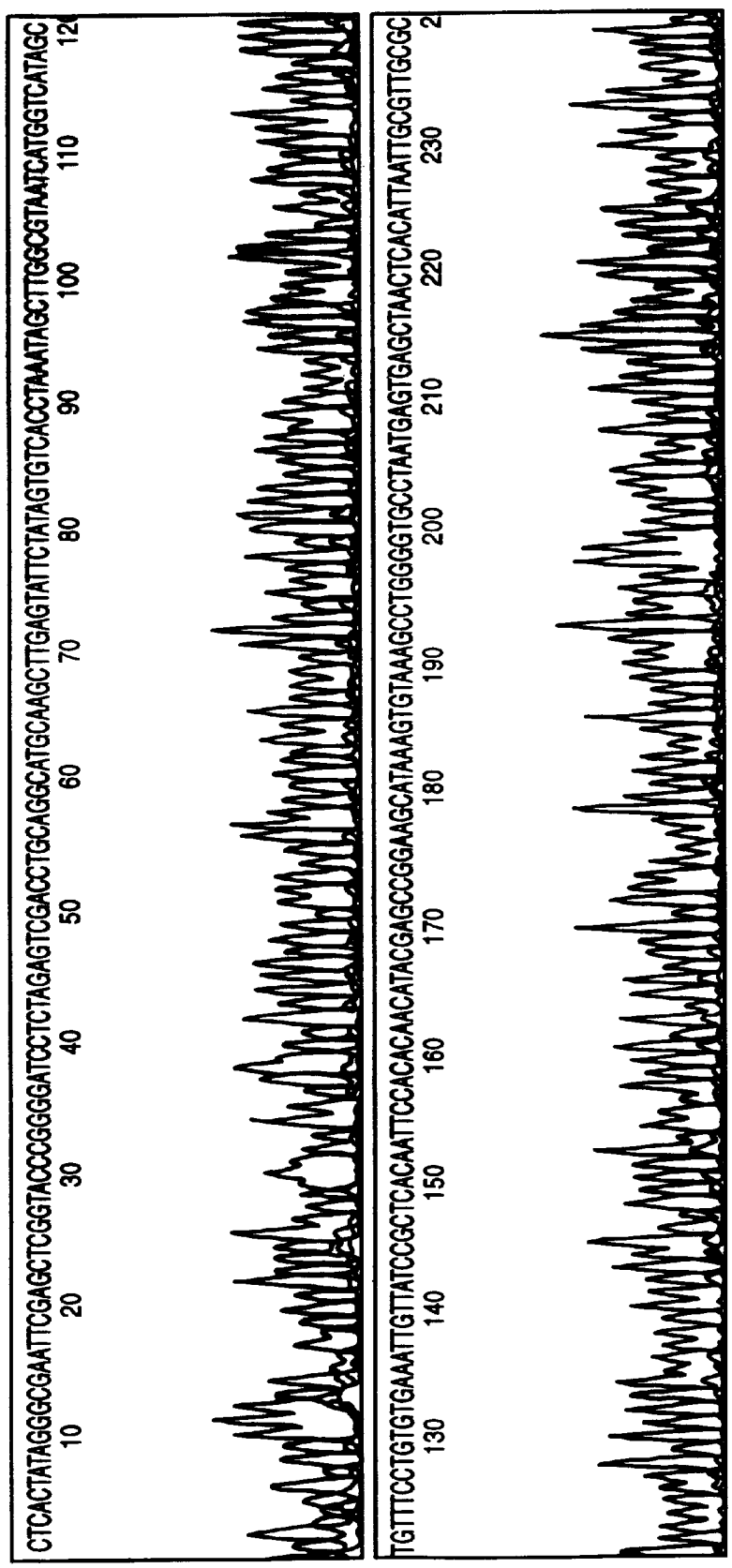

FIGS. 4(a), (b) and (c). This shows the results of dye-primer DNA sequencing with HiFi Bst Template: single-stranded pGEM-3Zf(+);

Primer: −21M13 forward DYEnamic Energy Transfer Dye Primers.

Figure 5A:
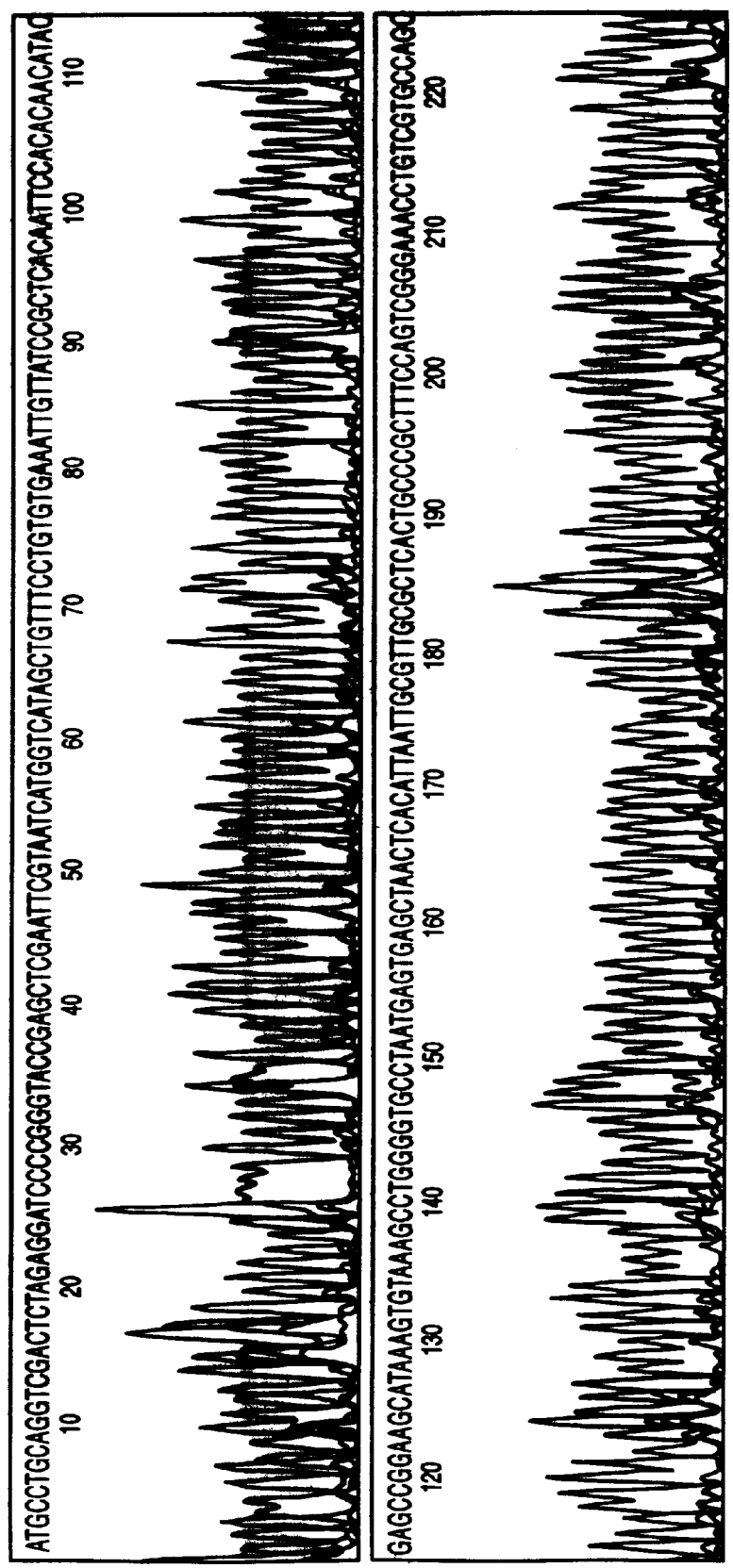

FIGS. 5(a), (b) and (c). This shows the results of dye-primer DNA sequencing with HiFi Bst-II.

Template: single-stranded M13mp18;

Primer: −21M13 forward DYEnamic Energy Transfer Dye Primers.

Figure 6A:
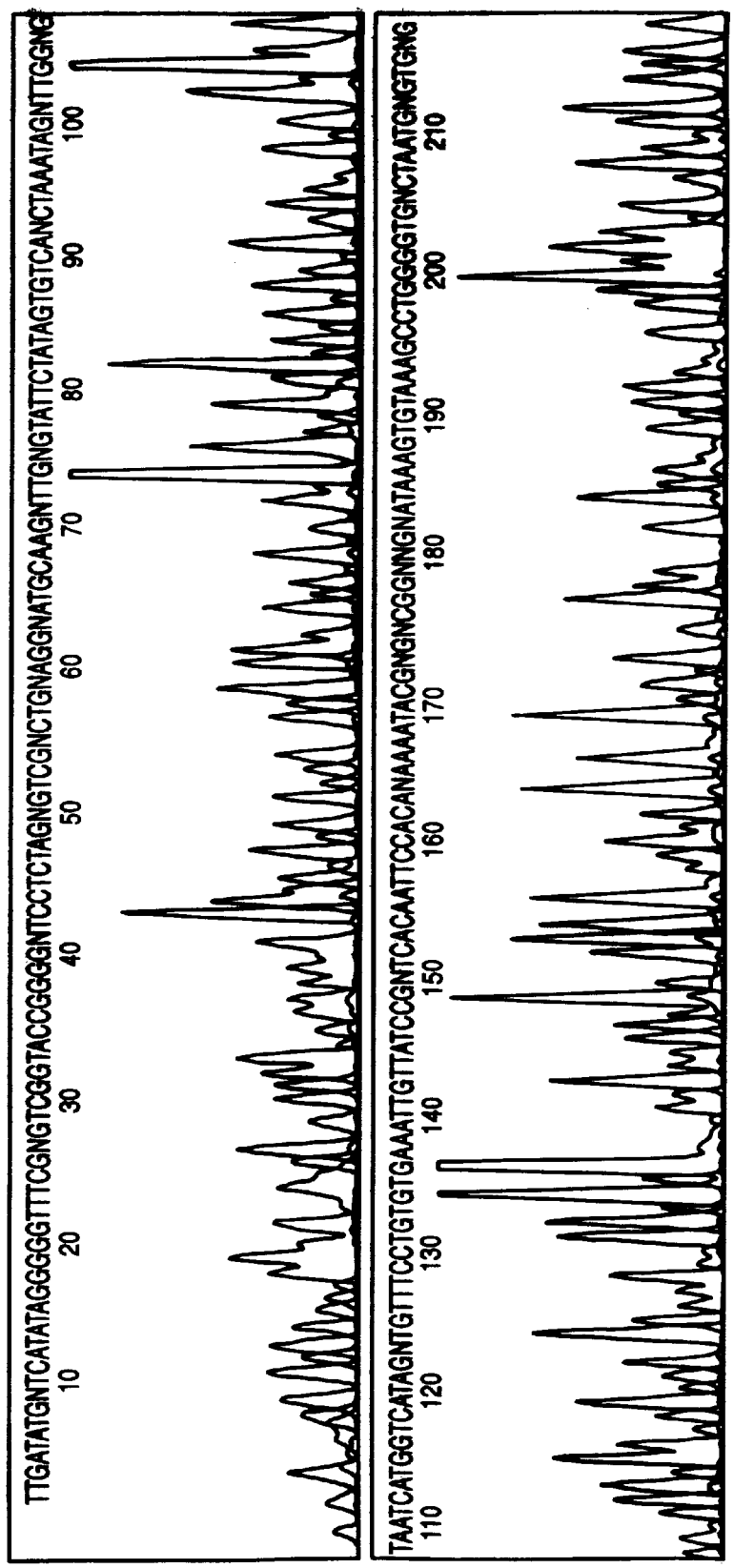

FIGS. 6(a), (b) and (c). This shows the results of dye-terminator DNA sequencing with HiFi Bst Template: single-stranded pGEM-3Zf(+);

Primer: −20M13 forward primer.

Figure 7A:
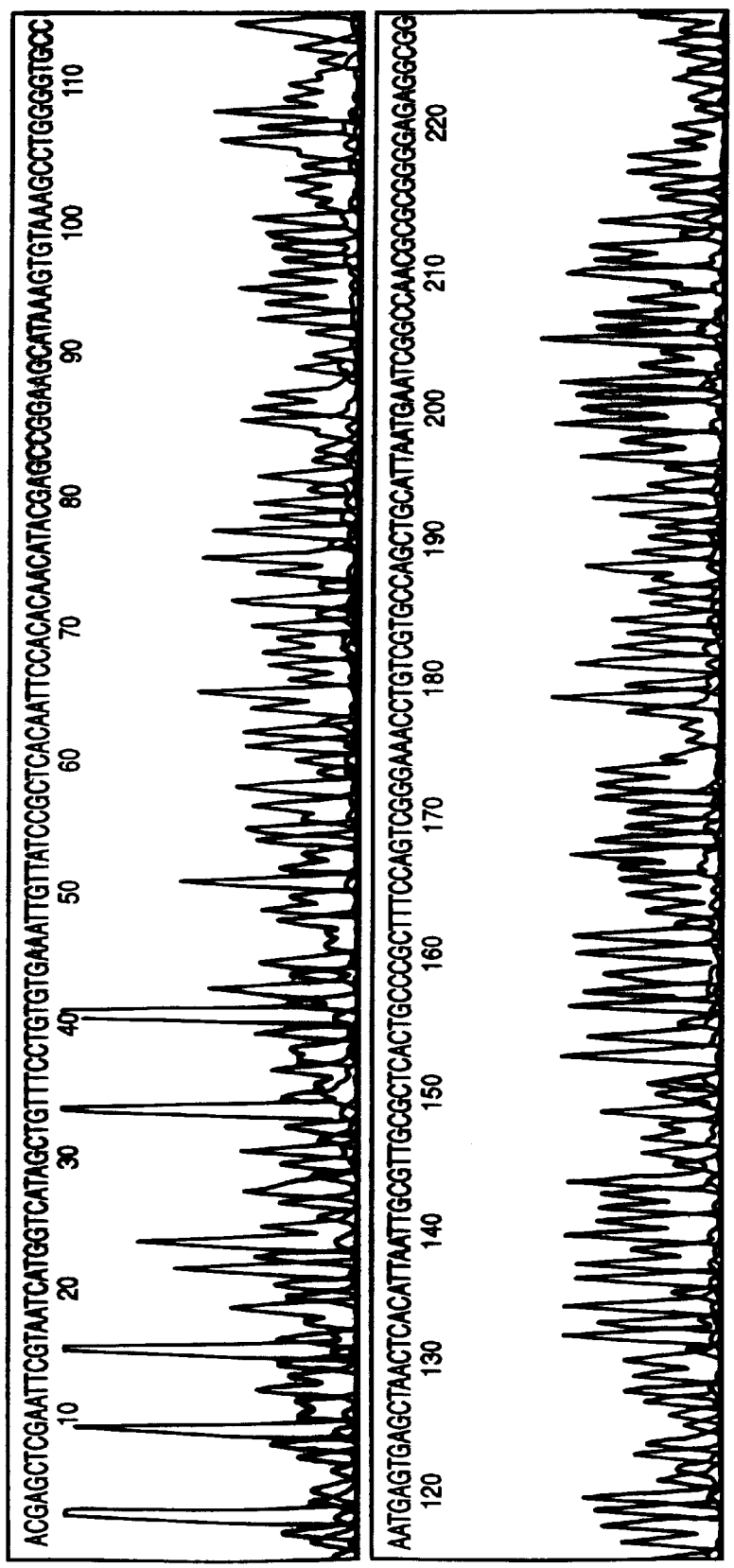

FIGS. 7(a), (b) and (c). This shows the results of dye-terminator DNA sequencing with HiFi Bst-II.

Template: single-stranded M13mp18;

Primer: −20M13 forward primer.

Figure 8A:
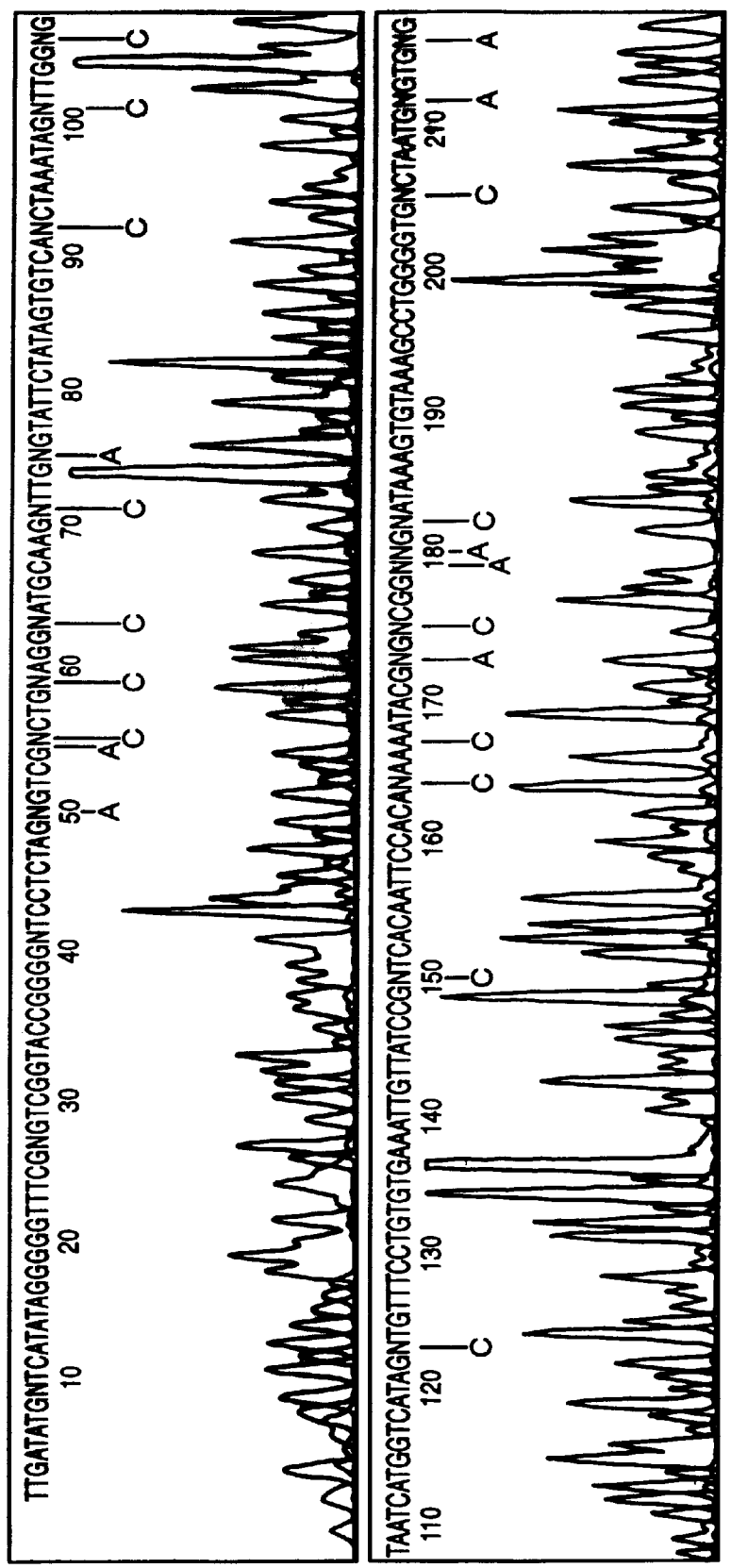
Figure 8B:
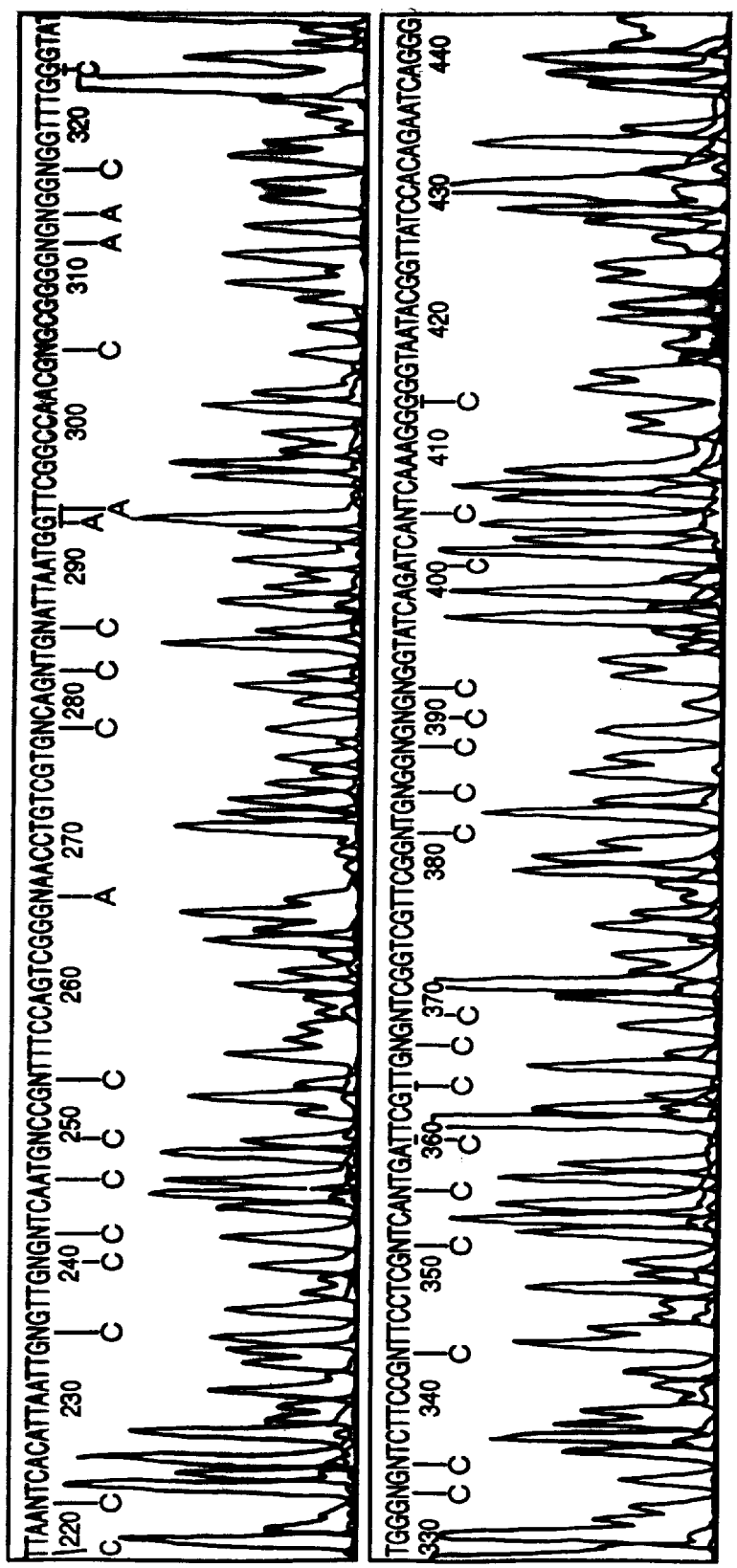
Figure 8C:
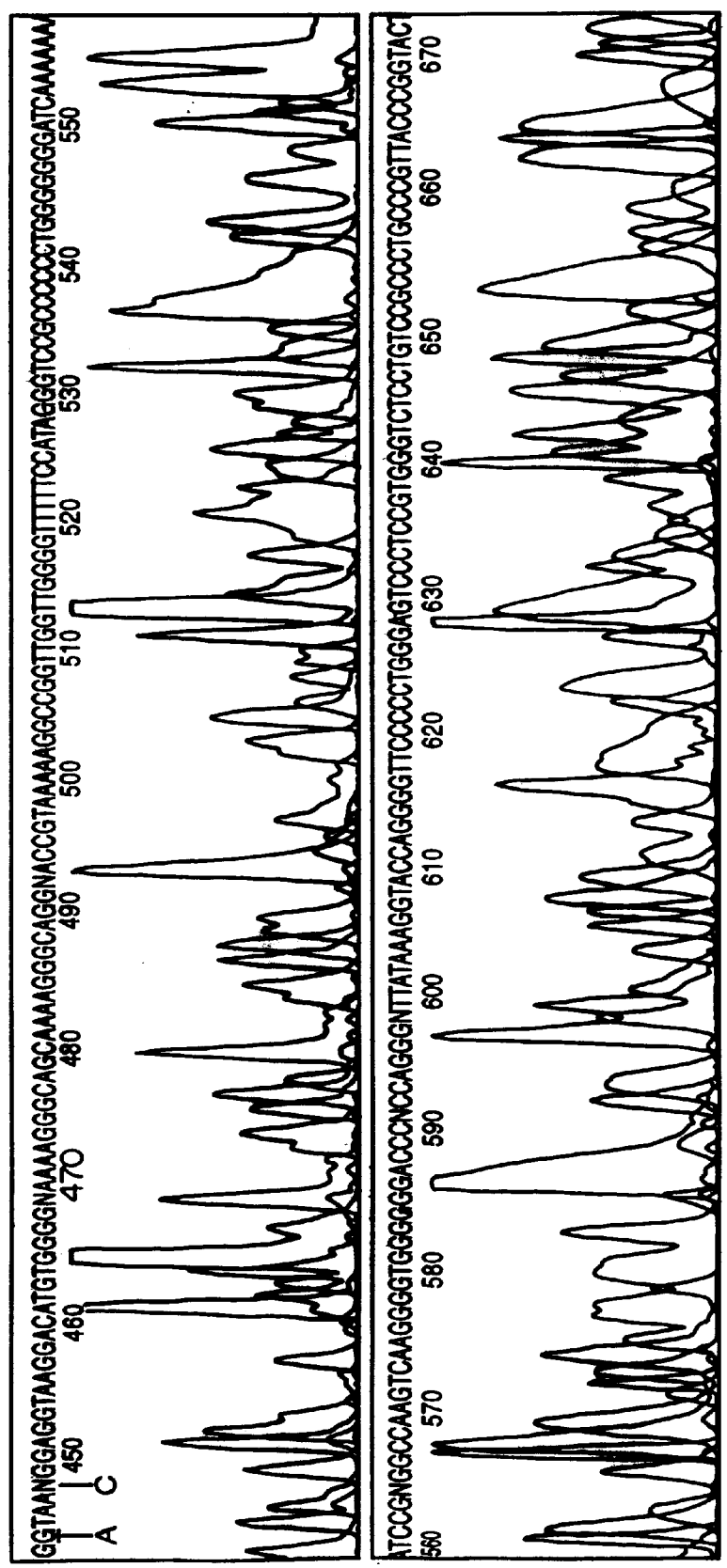

FIGS. 8(a), (b) and (c). Like FIG. 6, this shows the results of four fluorescent dye-labeled terminators DNA sequencing with HiFi Bst. In FIG. 8 corrections of the missing or ambiguous bases, according to the known PGEM sequence, are indicated below the letters "N" or below the incorrect base letters.

Template: single-stranded pGEM-3Zf(+);

Primer: −20M13 forward primer.

DETAILED DESCRIPTION OF THE INVENTION

The DNA polymerases of the invention are capable of reducing selective discrimination against incorporation of fluorescent dye-labeled dideoxynucleotide terminators ddCTP and ddATP, (but not ddGTP and ddTTP), in the presence of adequate amounts of dNTPs and the four terminators.

The inventors discovered that certain modifications of the amino acid sequence of DNA polymerases (i.e., modifying the amino acids at positions 342–344 to substitute threonine, proline and leucine, respectively, for leucine, glutamate and glutamate, and modifying the amino acid at position 422 to substitute tyrosine for phenylalanine, as corresponding to the amino acid sequence of Bst 320 DNA polymerase) result in a marked reduction of the innate selective discrimination against incorporation of fluorescent dye-labeled dideoxy-nucleotide ddCTP and ddATP, that is characteristic of the unmodified DNA polymerase. This reduction of selective discrimination can be demonstrated by direct automated fluorescent terminator DNA sequencing as recovered missing or ambiguous "C" peaks and/or "A" peaks in the automated sequencing results, using a known template as standard.

The preferred source for the DNA polymerase is *Bacillus stearothermophilus* because DNA polymerase isolated from this mesophilic bacillus is highly processive, can be used and stored in dried down form, has an optimum temperature at 65° C., and can be used for direct DNA sequencing without precycling. The preferred Bst DNA polymerase is that isolated from strain 320 with an amino acid sequence as follows:

Amino acid sequence (SEQ ID NO:2):

| | | | |
|---|---|---|---|
| AEGEKPLEEM | EFAIVDVITE | EMLADKAALV | VEVMEENYHD |
| APIVGIALVN | EHGRFFMRPE | TALADSQFLA | WLADETKKKS |
| MFDAKRAVVA | LKWKGIELRG | VAFDLLLAAY | LLNPAQDAGD |
| IAAVAKMKQY | EAVRSDEAVY | GKGVKRSLPD | EQTLAEHLVR |
| KAAAIWALEQ | PFMDDLRNNE | QDQLLTKLEH | ALAAILAEME |
| FTGVNVDTKR | LEQMGSELAE | QLRAIEQRIY | ELAGQEFNIN |
| SPKQLGVILF | EKLQLPVLKK | TKTGYSTSAD | VLEKLAPHHE |
| IVENILHYRQ | LGKLQSTYIE | GLLKVVRPDT | GKVHTMFNQA |
| LTQTGRLSSA | EPNLQNIPIR | LEEGRKIRQA | FVPSEPDWLI |
| FAADYSQIEL | RVLAHIADDD | NLIEAFQRDL | DIHTKTAMDI |
| FQLSEEEVTA | NMRRQAKAVN | FGIVYGISDY | GLAQNLNITR |
| KEAAEFIERY | FASFPGVKQY | MENIVQEAKQ | KGYVTTLLHR |
| RRYLPDITSR | NFNVRSFAER | TAMNTPIQGS | AADIIKKAMI |
| DLAARLKEEQ | LQARLLLQVH | DELILEAPKE | EIERLCELVP |
| EVMEQAVTLR | VPLKVDYHYG | PTWYDAK | |

The characters represent the following amino acids:

| | | | |
|---|---|---|---|
| A: | alanine (Ala) | M: | methionine (Met) |
| C: | cysteine (Cys) | N: | asparagine (Asn) |
| D: | aspartic acid (Asp) | P: | proline (Pro) |
| E: | glutamic acid (Glu) | Q: | glutamine (Gln) |
| F: | phenylanaline (Phe) | R: | arginine (Arg) |
| G: | glycine (Gly) | S: | serine (Ser) |
| H: | histidine (His) | T: | threonine (Thr) |
| I: | isoleucine (Ile) | V: | valine (Val) |
| K: | lysine (Lys) | W: | tryptophan (Trp) |
| L: | leucine (Leu) | Y: | tyrosine (Tyr) |

The Bst 320 DNA polymerase is characterized by possessing a proofreading 3'-5' exonuclease activity.

The nucleotide sequence encoding the unmodified Bst 320 DNA polymerase is indicated in SEQ ID NO:1, in Example 2 below.

The following amino acid sequence represents the modified Bst 320 DNA polymerase as the preferred embodiment of this invention, modified from the naturally-occurring Bst 320 DNA polymerase at positions 342–344 to substitute threonine, proline and leucine, respectively, for leucine, glutamate and glutamate, and at position 422 to substitute tyrosine for phenylalanine.

Amino acid sequence (SEQ ID NO:4): MAEGEKPLEEMEFAIVDVITEEMLAD-KAALVVEVMEENYHDAPIV GIALVNEHGRFFMR-PETALADSQFLAWLADETKKKSMFDAKRAVV ALKWKGIELRGVAFDLLLAAYLLN-PAQDAGDIAAVAKMKQYEAVR SDEAVYGKGVKRSLPDEQTLAEHLVR-KAAAIWALEQPFMDDLRNN EQDQLLTKLEHA-LAAILAEMEFTGVNVDTKRLEQMGSELAEQLRA IEQRIYELAGQEFNINSPKQLGVILFEK-LQLPVLKKTKTGYSTSA DVLEKLAPHHEIVENIL-HYRQLGKLQSTYIEGLLKVVRPDTGKVH TMFN-QALTQTGRLSSAEPNLQNIPIR TPLGRKIRQAFVPSEPDWL IFAADYSQIELRVLAHI-ADDDNLIEAFQRDLDIHTKTAMDIFQLS EEEVTANM-RRQAKAVNYGIVYGISDYGLAQNLNITRKEAAEFIER YFASFPGVKQYMENIVQEAKQKGYVT-TLLHRRRYLPDITSRNFNV RSFAERTAMNTPIQGSAA-DIIKKAMIDLAARLKEEQLQARLLLQV HDELILEAP-KEEIERLCELVPEVMEQAVTLRVPLKVDYHYGPTWY DAK The underlined amino acids are substituted amino acids produced by site-directed mutation of the naturally-occurring Bst 320 DNA polymerase.

The modified Bst 320 DNA polymerase is encoded by a DNA sequence such as the following (SEQ ID NO:3):

```
                                              ATG
GCCGAAGGGG  AGAAACCGCT  TGAGGAGATG  GAGTTTGCCA
TCGTTGACGT  CATTACCGAA  GAGATGCTTG  CCGACAAGGC
AGCGCTTGTC  GTTGAGGTGA  TGGAAGAAAA  CTACCACGAT
GCCCCGATTG  TCGGAATCGC  ACTAGTGAAC  GAGCATGGGC
GATTTTTTAT  GCGCCCGGAG  ACCGCGCTGG  CTGATTCGCA
ATTTTTAGCA  TGGCTTGCCG  ATGAAACGAA  GAAAAAAGC
ATGTTTGACG  CCAAGCGGGC  AGTCGTTGCC  TTAAAGTGGA
GGTCGGATGA  AGCGGTCTAT  GGCAAAGGCG  TCAAGCGGTC
GCTGCCGGAC  GAACAGACGC  TTGCTGAGCA  TCTCGTTCGC
AAAGCGGCAG  CCATTTGGGC  GCTTGAGCAG  CCGTTTATGG
ACGATTTGCG  GAACAACGAA  CAAGATCAAT  TATTAACGAA
GCTTGAGCAC  GCGCTGGCGG  CGATTTTGGC  TGAAATGGAA
TTCACTGGGG  TGAACGTGGA  TACAAAGCGG  CTTGAACAGA
TGGGTTCGGA  GCTCGCCGAA  CAACTGCGTG  CCATCGAGCA
GCGCATTTAC  GAGCTAGCCG  GCCAAGAGTT  CAACATTAAC
TCACCAAAAC  AGCTCGGAGT  CATTTTATTT  GAAAAGCTGC
AGCTACCGGT  GCTGAAGAAG  ACGAAAACAG  GCTATTCGAC
TTCGGCTGAT  GTGCTTGAGA  AGCTTGCGCC  GCATCATGAA
```

```
                          -continued
ATCGTCGAAA  ACATTTTGCA  TTACCGCCAG  CTTGGCAAAC
TGCAATCAAC  GTATATTGAA  GGATTGTTGA  AAGTTGTGCG
CCCTGATACC  GGCAAAGTGC  ATACGATGTT  CAACCAAGCG
CTGACGCAAA  CTGGGCGGCT  CAGCTCGGCC  GAGCCGAACT
TGCAAAACAT  TCCGATTCGG  ACCCCACTGG  GGCGGAAAAT
CCGCCAAGCG  TTCGTCCCGT  CAGAGCCGGA  CTGGCTCATT
TTCGCCGCCG  ATTACTCACA  AATTGAATTG  CGCGTCCTCG
CCCATATCGC  CGATGACGAC  AATCTAATTG  AAGCGTTCCA
ACGCGATTTG  GATATTCACA  CAAAAACGGC  GATGGACATT
TTCCAGTTGA  GCGAAGAGGA  AGTCACGGCC  AACATGCGCC
GCCAGGCAAA  GGCCGTTAAC  TACGGTATCG  TTTACGGAAT
TAGCGATTAC  GGATTGGCGC  AAAACTTGAA  CATTACGCGC
AAAGAAGCTG  CCGAATTTAT  CGAACGTTAC  TTCGCCAGCT
TTCCGGGCGT  AAAGCAGTAT  ATGGAAAACA  TAGTGCAAGA
AGCGAAACAG  AAAGGATATG  TGACAACGCT  GTTGCATCGG
CGCCGCTATT  TGCCTGATAT  TACAAGCCGC  AATTTCAACG
TCCGCAGTTT  TGCAGAGCGG  ACGGCCATGA  ACACGCCAAT
TCAAGGAAGC  GCCGCTGACA  TTATTAAAAA  AGCGATGATT
GATTTAGCGG  CACGGCTGAA  AGAAGAGCAG  CTTCAGGCTC
GTCTTTTGCT  GCAAGTGCAT  GACGAGCTCA  TTTTGGAAGC
GCCAAAAGAG  GAAATTGAGC  GATTATGTGA  GCTTGTTCCG
GAAGTGATGG  AGCAGGCCGT  TACGCTCCGC  GTGCCGCTGA
AAGTCGACTA  CCATTACGGC  CCAACATGGT  ATGATGCCAA
A
```

The characters represent the following nucleotides:
A: Adenosine T: Thymidine
C: Cytidine G: Guanosine The underlined nucleotides are substituted nucleotides produced by site-directed mutation of the naturally-occurring Bst 320 polymerase. (As would be apparent to someone skilled in this art, this DNA sequence does not indicate the starting codon.)

The invention also contemplates any DNA sequence that is complementary to the modified Bst 320 DNA sequence, for instance, DNA sequences that would hybridize to the above DNA sequence of the modified DNA polymerase under stringent conditions. As would be understood by someone skilled in the art, the invention also contemplates any DNA sequence that encodes a peptide having these characteristics and properties (including degenerate DNA code).

This invention also contemplates allelic variations and mutations (for instance, adding or deleting nucleotide or amino acids, sequence recombination or replacement or alteration) which result in no substantive change in the function of the DNA polymerase or its characteristics. For instance, the DNA polymerases encompass non-critical substitutions of nucleotides or amino acids that would not change functionality (i.e., such as those changes caused by a transformant host cell). In addition, the invention is intended to include fusion proteins and muteins of the unique DNA polymerases of this invention.

The DNA sequences and amino acid sequences for the modified DNA polymerase of this invention are also obtainable by, for instance, isolating and purifying DNA polymerase from a *Bacillus stearothermophilus*, or a bacterial strain otherwise derived from *Bacillus stearothermophilus*, or other mesophilic bacillus strains such as *Bacillus caldotenax* or *Bacillus caldolyticus*. The DNA polymerases obtained from these organisms may be easily modified using conventional DNA modification techniques to achieve the reduction in fluorescent dye-labeled ddCTP and ddATP selective discrimination, as long as the unmodified amino acid sequences have leucine-glutamate-glutamate at positions corresponding respectively to positions 342–344 of Bst 320 DNA polymerase and phenylalanine at a position corresponding to position 422 of Bst 320 DNA polymerase. For instance, using the primers and methods of screening described herein, someone skilled in the art could isolate a DNA polymerase having the same properties and function from other strains.

In the DNA polymerases currently used in conventional DNA sequencing protocols, it is preferred that the enzymes have low or no exonuclease activity. However, in this invention, it is preferred that the DNA polymerases have a function of high fidelity ("HiFi") nucleotide incorporation. Therefore, in one preferred embodiment the invention entails modification of a naturally-occurring Bst DNA polymerase having a proofreading 3'-5' exonuclease activity. This preferred modified DNA polymerase (e.g., "HiFi Bst-II") has a nucleotide sequence indicated in SEQ ID:NO 3 and an amino sequence indicated in SEQ ID:NO 4. To initially obtain a Bst DNA polymerase having proofreading 3'-5' activity, strains of *Bacillus stearothermophilus* can be segregated into different groups according to the proof-reading exonuclease activity of their respective DNA polymerases.

The invention also provides a DNA construct comprising at least one of the DNA sequences of the modified DNA polymerase and a vector (such as a cloning vector or an expression vector), for introducing the DNA construct into host cells. An example of a suitable vector is pYZ23/LF, described below.

The host cells need only be capable of being stably transformed with the DNA construct in a manner allowing production of the peptide encoded by the DNA segment in the construct (preferably in large quantity). The host cells may be of eucaryotic or procaryotic origin (such as a *E. coli* host cell). For instance, the host cell may be a mesophilic organism, although this is not a necessary requirement in order that a host cell be effective.

The invention also provides improved methods for DNA sequencing using the above-described novel DNA polymerases. The methods entail sequencing a DNA strand by conventional protocols with the following modifications:

i) hybridizing a primer to a DNA template to be sequenced;
ii) extending the primer using a DNA polymerase described above, in the presence of radiolabeled DATP, nucleotides dGTP, dCTP and dTTP, or their analogs, and ddNTP chain terminators; and
iii) allowing a DNA strand to be sequenced.

All four dNTPs, including dCTP, are incorporated equally effectively in the chain elongation during sequencing reaction catalyzed by the DNA polymerases of the invention with a high processivity and a high elongating rate.

Preferably the nucleotide premix concentrations of modified Bst DNA polymerase used in radiolabeled DNA sequencing are as following:

A mix: DATP 0.8 µM, dCTP 80 µM, dGTP 80 µM, dTTP 80 µM, ddATP 25 µM;
C mix: DATP 0.8 µM, dCTP 8 µM, dGTP 80 µM, dTTP 80 µM, ddCTP 20 µM;
G mix: DATP 0.8 µM, dCTP 80 µM, dGTP 8 µM, dTTP 80 µM, ddGTP 50 µM;
T mix: dATP 0.8 µM, dCTP 80 µM, dGTP 80 µM, dTTP 8 µM, ddTTP 50 µM. (This mixture is useful for the particular modified Bst 320 DNA polymerase set forth above, as well as for other modified Bst DNA polymerases.)

In addition, the invention contemplates other uses of the modified DNA polymerases. For instance, the DNA polymerase can also be use in (1) filling-in 5' overhangs of DNA fragments; (2) synthesis of DNA probes by random primers labeling methodology; and (3) site-directed mutagenesis.

The following non-limiting examples are illustrative of the invention.

EXAMPLE 1

Screening for Bst polymerases

This invention also involves a method to measure the proof-reading 3'-5' exonuclease activity of purified DNA polymerases. The method is useful to screen a large number of bacterial strains, such as *Bacillus stearothermophilus* and other mesophilic bacterial strains, to select a strain which produces a DNA polymerase with a high proof-reading 3'-5' exonuclease activity. For instance, the method to test the proof-reading 3'-5' exonuclease activity of DNA polymerase was carried out as follows.

A DNA primer and two DNA templates with following sequences were synthesized chemically, using a DNA synthesizer.

```
                                            (SEQ ID NO:5)
17-base primer   5' CATTTTGCTGCCGGTCA 3'

1 mg/ml (SEQ ID NO:6)
Template (a)   3'------GTAAAACGACGGCCAGTCTT------5'

10 mg/ml (SEQ ID NO:7)
Template (b)   3'-----GTAAAACGACGGCCAGTCGG-----5'

10 mg/ml
```

To produce the radiolabeled primer, 1 µl (1 µg) of primer, 5 µl (50 µg) of template (a), 1 µl of [α-$^{32}$P] DATP (800 Ci/mmole), 1 µl of dGTP (0.5 mM), 1 µl of Taq DNA polymerase (1 unit), and 1 µl of buffer consisting of 500 mM Tris-Cl, pH 9.0, and 150 mM MgCl$_2$, were mixed in a test tube and incubated in a 65° C. water bath for 5 minutes. The mixture was subject to alkaline denaturing gel electrophoresis. The radioactive band containing the 20-base nucleotide was isolated and dissolved in 12 µl of 10 mM Tris-Cl buffer, containing 1 mM EDTA, pH 8.0. The final product represents the following labeled 20-base primer.

```
    5' CATTTTGCTGCCGGTCAGA*A*  3'    (SEQ ID NO:8)

(* = 32P labeled)
```

To produce radiolabeled primer-template complexes, 5 μl of the labeled primer was mixed with 10 μl of template (a) or template (b) respectively to form the following:

```
Complex (a)

5'CATTTTGCTGCCGGTCAGA*A* 3'  (same as SEQ ID NO:8)

3'GTAAAACGACGGCCAGTCT T   5'  (same as SEQ ID NO:6)

Complex (b)

5' CATTTTGCTGCCGGTCAGA*A* 3'  (same as SEQ ID NO:8)

3' GTAAAACGACGGCCAGTCG G   5'  (same as SEQ ID NO:7)
```

The free radiolabeled primer was removed through a G-50 Sephadex column.

An aliquot of complex (a) which had two correctly matched radiolabeled A*s at the 3' terminus of the primer, and an aliquot of complex (b) which had two mismatched A*s at the 3' terminus of the primer, were then pipetted into two individual vials of scintillation fluid and their radioactivity was measured in a scintillation counter, and both complexes were adjusted with buffer to a concentration containing the same molarity of incorporated [$\alpha$-$^{32}$P] dAMp.

To perform the proof-reading 3'-5' exonuclease activity, 20 μl of complex (a) or complex (b), 8 μl reaction buffer consisting of 15 mM Tris-Cl and 15 mM MgCl$_2$, pH 8.5, 4 units of DNA polymerase, and enough water to make up a total volume of 40 μl were pipetted into a test tube and mixed well. The mixture was subdivided into aliquots of 3 μl each in 0.5 ml microcentrifuge tubes and was then covered with 3 μl paraffin in each tube. The microcentrifuge tubes were incubated in a 65° C. water bath. At 1, 2, 3, 5, 10, and 20 minutes, a pair of the microcentrifuge tubes were taken out from the water bath and the content of each tube was dotted onto a DE-81 Whatman filter paper. One of each pair of the filter papers was put in scintillation fluid directly and the radioactivity was counted in cpm value in a scintillation counter; the other was washed three times in 0.3 M sodium phosphate buffer, pH 6.8 before being put into the scintillation fluid for counting.

The difference in radioactivity expressed in cpm value between the washed filter paper and the unwashed filter paper in each pair was interpreted as representing the relative quantity of labeled nucleotides excised by the 3'-5' exonuclease activity from the 3' terminus of the primer. A DNA polymerase that excised the radiolabeled nucleotides A*s from complex (b) more efficiently than from complex (a) possessed proof-reading 3'-5' exonuclease activity. A DNA polymerase that excised the radiolabeled nucleotides A*s from complex (a) faster than from complex (b), or at nearly the same rate, was interpreted as possessing a non-specific 3'-5' exonuclease activity which is considered unsuitable for DNA sequencing.

Using these methods, a strain of bacteria was isolated from among the strains of *Bacillus stearothermophilus* from various sources which is distinguished in its fast growth rate. This strain reached an optimum exponential growth within 3 hours for DNA polymerase production. The strain was also able to produce a DNA polymerase with a proof-reading 3'-5' exonuclease activity. This strain of *Bacillus stearothermophilus* was labeled Bst No. 320.

As persons skilled in this art would appreciate, the bacterial strain, or even the strain of *Bacillus stearothermophilus*, from which a mesophilic DNA polymerase of the invention can be obtained may be derived using the above-described methods or others known in the art from strains of *Bacillus stearothermophilus* or other bacteria strains (especially mesophilic strains), including wild strains or mutant strains acquired by various means, including spontaneous mutation.

To prepare the preferred purified Bst DNA polymerase, the cells of Bst No. 320 were grown at 55° C. in a liquid medium consisting of 1% polypeptone, 0.5% yeast extract and 0.5% NaCl, pH7.0–7.2. The 3 hr old cells were collected after centrifugation and suspended in 4 volumes of TME buffer (50 mM Tris-HCl, pH7.5, 10 mM β-mercaptoethanol, and 2 mM EDTA), containing 100 mg lysozyme and 23 mg phenylmethylsulphonyl-fluoride/ml. The cells were broken by sonication in ice. The supernatant was pooled after centrifugation at 28,000 rpm in a Spinco L 30 rotor.

The purified Bst DNA polymerase of the invention was prepared according to Okazaki and Kornberg (7) with appropriate slight modifications and the large fragment of the DNA polymerase was obtained by partial digestion of the whole DNA polymerase with the proteinase subtilisin (type Carlsberg) basically according to Jacobsen et al. (8).

The procedure for purification of enzyme was followed as described in Ye and Hong (4). This Bst DNA polymerase possessed a proof-reading 3'-5' exonuclease activity.

The Bst polymerase was tested for proof-reading and non-specific 3'-5' exonuclease activities as described above. The results showed that the polymerase excised the mismatched incorporated nucleotides from the 3' terminus of a double-stranded DNA at a high rate, reaching the plateau of hydrolysis in about 3 minutes, about 8 times more efficiently in the first 3 minutes of reaction than those correctly matched with the nucleotides of the template. This enzyme is referred to herein as HiFi Bst DNA polymerase, and is distinguishable from Bst DNA polymerases isolated from other strains of *Bacillus stearothermophilus*.

This prodedure of using HiFi Bst as the DNA polymerase in the classic radiolabeling Sanger reaction for DNA sequencing and its autoradiograph are illustrated in Example 8. The data obtained by adapting this procedure to use HiFi Bst as the DNA polymerase in dye-labeled primer automated fluorescent DNA sequencing are illustrated in Example 9. These results indicate that HiFi Bst DNA polymerase can be used for the classic Sanger manual sequencing and the fluorescent dye-labeled primer sequencing with high processivity and high fidelity.

However, when the protocol was modified for fluorescent dye-labeled ddNTP terminator automated DNA sequencing, numerous "C" peaks and "A" peaks were missing or appeared ambiguous in the sequence plot, especially when the "C" peak was immediately after a "G" peak or after an "A" peak, and when the "A" peak was immediately after a "G" peak. This selective discrimination against incorporation of dye-labeled ddCTP and dye-labeled ddATP is sequence-related since many "C" and "A" peaks following an immediate "C" peak or an immeciate "T" peak remained strong and correctly resolved in the same color plot of sequence analysis. (See Example 9) This phenomenon of selective discrimination against incorporation of fluorescent dye-labeled ddCTP and dye-labeled ddATP is observed with all DNA polymerases isolated from different strains of *Bacillus stearothermophilus* and *Bacillus caldotenax*, and appears to be characteristic of DNA polymerases of the mesophilic bacilli.

EXAMPLE 2

Mutation of the gene for naturally-occurring Bst DNA polymerase having proofreading 3'-5' exonuclease activity The DNA fragment LF containing the gene initially isolated from the wild Bst 320 has the following sequence (see SEQ ID NO:1):

```
GCCGAAGGGG  AGAAACCGCT  TGAGGAGATG  GAGTTTGCCA
TCGTTGACGT  CATTACCGAA  GAGATGCTTG  CCGACAAGGC
AGCGCTTGTC  GTTGAGGTGA  TGGAAGAAAA  CTACCACGAT
GCCCCGATTG  TCGGAATCGC  ACTAGTGAAC  GAGCATGGGC
GATTTTTTAT  GCGCCCGGAG  ACCGCGCTGG  CTGATTCGCA
ATTTTTAGCA  TGGCTTGCCG  ATGAAACGAA  GAAAAAAGC
ATGTTTGACG  CCAAGCGGGC  AGTCGTTGCC  TTAAAGTGGA
AAGGAATTGA  GCTTCGCGGC  GTCGCCTTTG  ATTTATTGCT
CGCTGCCTAT  TTGCTCAATC  CGGCTCAAGA  TGCCGGCGAT
ATCGCTGCGG  TGGCGAAAAT  GAAACAATAT  GAAGCGGTGC
GGTCGGATGA  AGCGGTCTAT  GGCAAAGGCG  TCAAGCGGTC
GCTGCCGGAC  GAACAGACGC  TTGCTGAGCA  TCTCGTTCGC
AAAGCGGCAG  CCATTTGGGC  GCTTGAGCAG  CCGTTTATGG
ACGATTTGCG  GAACAACGAA  CAAGATCAAT  TATTAACGAA
GCTTGAGCAC  GCGCTGGCGG  CGATTTTGGC  TGAAATGGAA
TTCACTGGGG  TGAACGTGGA  TACAAAGCGG  CTTGAACAGA
TGGGTTCGGA  GCTCGCCGAA  CAACTGCGTG  CCATCGAGCA
GCGCATTTAC  GAGCTAGCCG  GCCAAGAGTT  CAACATTAAC
TCACCAAAAC  AGCTCGGAGT  CATTTTATTT  GAAAAGCTGC
AGCTACCGGT  GCTGAAGAAG  ACGAAAACAG  GCTATTCGAC
TTCGGCTGAT  GTGCTTGAGA  AGCTTGCGCC  GCATCATGAA
ATCGTCGAAA  ACATTTTGCA  TTACCGCCAG  CTTGGCAAAC
TGCAATCAAC  GTATATTGAA  GGATTGTTGA  AAGTTGTGCG
CCCTGATACC  GGCAAAGTGC  ATACGATGTT  CAACCAAGCG
CTGACGCAAA  CTGGGCGGCT  CAGCTCGGCC  GAGCCGAACT
TGCAAAACAT  TCCGATTCGG  CTCGAAGAGG  GGCGGAAAAT
CCGCCAAGCG  TTCGTCCCGT  CAGAGCCGGA  CTGGCTCATT
TTCGCCGCCG  ATTACTCACA  AATTGAATTG  CGCGTCCTCG
CCCATATCGC  CGATGACGAC  AATCTAATTG  AAGCGTTCCA
ACGCGATTTG  GATATTCACA  CAAAAACGGC  GATGGACATT
TTCCAGTTGA  GCGAAGAGGA  AGTCACGGCC  AACATGCGCC
GCCAGGCAAA  GGCCGTTAAC  TTCGGTATCG  TTTACGGAAT
TAGCGATTAC  GGATTGGCGC  AAAACTTGAA  CATTACGCGC
AAAGAAGCTG  CCGAATTTAT  CGAACGTTAC  TTCGCCAGCT
TTCCGGGCGT  AAAGCAGTAT  ATGGAAAACA  TAGTGCAAGA
AGCGAAACAG  AAAGGATATG  TGACAACGCT  GTTGCATCGG
CGCCGCTATT  TGCCTGATAT  TACAAGCCGC  AATTTCAACG
TCCGCAGTTT  TGCAGAGCGG  ACGGCCATGA  ACACGCCAAT
TCAAGGAAGC  GCCGCTGACA  TTATTAAAAA  AGCGATGATT
GATTTAGCGG  CACGGCTGAA  AGAAGAGCAG  CTTCAGGCTC
```
```
                            -continued
GTCTTTTGCT  GCAAGTGCAT  GACGAGCTCA  TTTTGGAAGC
GCCAAAAGAG  GAAATTGAGC  GATTATGTGA  GCTTGTTCCG
GAAGTGATGG  AGCAGGCCGT  TACGCTCCGC  GTGCCGCTGA
AAGTCGACTA  CCATTACGGC  CCAACATGGT  ATGATGCCAA
ATAA      (1764 nucleotides total)
```

Site directed mutagenesis was performed as described by Kunkel et al.(14) The DNA fragment (designated "LF") containing the gene for Bst DNA polymerase having proof-reading exonuclease activity was cloned from the expression vector pYZ23/LF into plasmid pUC119. The constructed plasmid pUC119/LF was then transformed into E. coli CJ236, a mutant of E. coli that lacks the enzymes dUTPase and uracil N-glycosylase. Therefore, when grown in a medium supplemented with uridine, this mutant of E. coli as well as the plasmids in the cells will incorporate deoxyuridine into the DNA in place of thymidine and the uracils will not be removed readily.

As the constructed plasmid grew in the cells of E. coli CJ236 and in the presence of uracil and M13KO7 helper phage, some of the normal thymidine bases of the DNA in the newly produced single-stranded pUC119/LF were replaced by uracils. These uracil-containing DNAs were used as the template in vitro for the production of a complementary oligonucleotide that contained the desired DNA sequence alteration, but with only dTMPs and not dUMP residues.

In practice, the expression vector pYZ23/LF was digested with restriction enzymes Eco RI and Bam HI, and the DNA fragment LF was separated and cloned into plasmid pUC119 which had been previously digested with the same restriction enzymes. The constructed plasmid pUC119/LF was then transformed into E. coli CJ236. For gaining the uracil-containing single-stranded pUC119/LF, a colony of E. coli CJ236 containing pUC119/LF was selected and inoculated into 2 ml of 2×YT medium which was supplemented with 0.25 ug/ml of uridine and $2 \times 10^8$ to $4 \times 10^8$ pfu/ml of M13KO7 as helper phage. After incubation at 37° C. with strong agitation for 1 hour, a kanamycin solution (25 mg/ml in $H_2O$) was added to the culture to a final concentration of 70 ug/ml. The incubation was allowed to continue for another 14–18 hours at 37° C. with strong agitation. Then 1.5 ml of the infected culture was transferred to a microcentrifuge tube, and centrifuged at 12,000×g for 5 minutes at 4° C. The uracil-containing single-stranded pUC119/LF was precipitated and purified from the supernatant according to standard PEG/NaCl and ethanol procedures.

After performing a series of experiments, the inventors found that the combined effects of changing the amino acids leucine-glutamate-glutamate (LEE) at the location 342–344, to respectively threonine-proline-leucine (TPL), and the amino acid phenylalanine (F) at location 422, to tyrosine (Y) in the peptide structure of HiFi Bst DNA polymerase markedly reduced its selective discrimination against incorporation of fluorescent dye-labeled ddCTP and dye-labeled ddATP to such a level that direct automated fluorescent DNA sequence (although not cycle-sequencing) can be performed with the dye-terminator technology when the mutated enzyme of the current invention is used. It is of interest to note that this modified HiFi Bst, now referred to as HiFi Bst-II DNA polymerase, exhibits the function of preferentially incorporating more fluorescent dye-labeled ddCTP and dye-labeled ddATP onto the 3' end dGMP and the dAMP bases of the extending DNA strands during enzymatic reaction, than the unmodified naturally occurring HiFi Bst polymerase.

The end result is the recovery of the "C" and "A" peaks which otherwise would have been missing or ambiguous on the sequence analysis color plot. At the same time, the modified enzyme did not indiscriminately generate an excess amount of dye-labeled "G" terminated or dye-labeled "T" terminated DNA fragments. Even the "C" and "A" peaks were not uniformly raised in a blanket manner, but only raised in the formerly depressed locations after a "G" and/or an "A". (See Example 9). Thus, this genetic modification of the HiFi Bst to HiFi Bst-II results in a DNA polymerase that reduces the selective discrimination against incorporation of the fluorescent dye-labeled ddCTP and dye-labeled ddATP, rather than merely increases the ability of the parent enzyme to incorporate these dye-labeled dideoxynucleotides.

HiFi Bst-II, and the other novel similar DNA polymerases of this invention, can be used for the classic radiolabeling Sanger method. (See Example 8.) HiFi Bst-II appears to generate a better sequencing pattern than HiFi Bst and requires less ddNTPs to terminate the extending reaction (FIG. 3). For instance, in the optimized reaction mixture for the unmodified HiFi Bst DNA polymerase, the ddNTP/dNTP ratios in the A, C, G and T mix were 40, 6.25, 18.25 and 18.72, respectively. In the optimized reaction mixture for the modified HiFi Bst-II DNA polymerase, the corresponding ddNTP/dNTP ratios in the A, C, G and T mix were 40, 2.5, 6.25 and 6.25, respectively. Therefore, there was an up-to about three-fold reduction in the amount of ddNTPs used after genetic modification of the naturally-occurring DNA polymerase.

For the radiolabeling classic Sanger method of DNA sequencing, the optimized reaction mixtures for either HiFi Bst or HiFi Bst-II must contain much more ddNTPs than dNTPs to generate a ladder of DNA fragments for sequencing analysis because the DNA polymerases of the mesophilic bacilli tend to incorporate dNTPs more efficiently than ddNTPs. The above-described genetic modification appears to increase the ability of the naturally-occurring enzymes to incorporate ddNTP in the presence of a corresponding competing dNTP to about three-fold at the concentration ratios commonly used for DNA sequencing. However, if much higher concentrations of the nucleotides were used for the experiment, and the ddNTP/dNTP ratio was reduced to a level that is suboptimal for DNA sequencing (for instance at a ratio of ⅓), the increased ability for incorporating ddNTPs after modification of the enzyme could be dramatized. (See Example 6, FIG. 2).

Similar to the results obtained with radiolabeling Sanger method, both HiFi Bst and HiFi Bst-II can be adapted for fluorescent dye-labeled primer automated DNA sequencing and produce comparable results without selective suppression of any specific fluorescent peaks in the sequencing plot (see Example 9) although the peaks generated by HiFi Bst-II appear to be more even than those by HiFi Bst.

To change amino acids leucine, glutamic acid and glutamic acid (LEE) at positions 342–344, respectively in the Bst polymerase into threonine, proline and leucine (TPL), respectively, Primer 1 was designed as following (see SEQ ID NO 10):

5'-CATTCCGATTCGG ACCCCACTGGGGCGGAAAATCCG-3

To change amino acid phenylalanine (F) at position 422 in the Bst DNA polymerase into tyrosine (Y), Primer 2 was designed as following (see SEQ ID NO: 9):

5'-GCCGTTAACTACGGTATCGTTTACGG-3'

After phosphorylation of the 5' ends of the oligonucleotides by T4 polynucleotide kinase, the two primers designed above were annealed to the single-stranded uracil-containing pUC119/LF purified from above. In the presence of the usual dNTPs (DATP, dCTP, dGTP and dTTP), T4 DNA polymerase was used to synthesize in vitro the strands of DNA complementary to the uracil-containing pUC119/LF template, and T4 ligase was used to ligate the synthesized strands to form a complete double-stranded plasmid which was composed of one single-stranded, not mutagenic, uracil-containing pUC119/LF and one complementary single-stranded, mutagenic, thymidine-containing DNA fragment that had been altered by primer 1 and primer 2 described above. These newly formed double-stranded plasmids were then transformed into E. coli JM109. The template strand was rendered biologically inactive. The transformed strain of E. coli JM109 whose plasmids contained the mutated DNA, now referred to as pUC119/LF-M, was screened out with DNA sequencing of its plasmids.

EXAMPLE 3

Cloning and expression of the modified Bst DNA polymerase having both ability to reduce selective dye labeled ddNTP discrimination and proofreading 3'5' exonuclease activity The plasmid pUC119/LF-M was prepared from the strain of Escherichia coli JM109 containing the mutated DNA. The mutated DNA fragment (LF-M) containing the mutated gene for the Bst polymerase was recombined back into the expression vector pYZ23. The constructed plasmid pYZ23/LF-M was then transformed into Escherichia coli JF1125. The mutation was further confirmed by double-stranded dideoxy DNA sequencing of isolated plasmid.

The strain of Escherichia coli JF1125 containing pYZ23/LF-M was inoculated into LB culture containing 100 µg/ml ampicillin, and was incubated overnight at 30° C. The overnight culture was inoculated into a large volume of fresh culture, and was incubated at 30° C. until the $OD_{600}$ of the culture reached 0.7. The culture was then heated at 41° C. for 3 hours for induction. The SDS-PAGE analysis of the cell extract showed that the cloned mutated gene for the modified Bst DNA polymerase was overexpressed.

EXAMPLE 4

Isolation and purification of the modified Bst DNA polymerase having both ability to reduce selective dye labeled ddNTP discrimination and proofreading 3'-5' exonuclease activity The expressed cells of Escherichia coli JF1125 containing pYZ23/LF-M grown in condition as described above were thawed and washed with buffer [10 mM Tris-HCl(pH7.5 at room temperature), 10 mM β-Mercaptoethanol, 2 mM EDTA, 0.9% NaCl]. The pellets were then suspended in buffer [50 mM Tris-HCl (pH7.5 at room temperature), 10 mM β-Mercaptoethanol, 2 mM EDTA, 100 µg/ml Lysozyme, 23 µg/ml PMSF] (4 ml/g pellet). After 20 min at room temperature, the mixture was cooled on salt-ice and sonicated briefly to complete lysis. The cell extract obtained by centrifugation at 18,000 rpm at 4° C. for 20 minutes, was then treated step by step as follows:

(A) The cell extract was heated at 60° C. for 30 minutes, and cooled to 4° C., then centrifuged at 15,000 rpm at 4° C. for 20 minutes;

(B) 5% Polymin P was added into supernatant to 0.6%, and mixed quickly for 30 minutes, then centrifuged;

(C) The pellet was resuspended in Buffer A [50 mM Tris-HCl(pH7.5 at room temperature), 1 mM EDTA, 1 mM β-Mercaptoethanol] containing 800 mM NaCl and 5% Glycerol at 4° C., and then centrifuged;

(D) Ammonium sulfate was added into the supernatant to 60% saturation at 4° C., and mixed for 30 minutes, then centrifuged;

(E) The ammonium sulfate pellet was resuspended in 30 ml of 60% saturated ammonium sulfate at 4° C., and then recentrifuged;

(F) The pellet was suspended in Buffer A containing 100 mM KCl and dialysed against the same buffer for hours at 4° C., then centrifuged. The insoluble protein was discard;

(G) The supernatant was added to pass through a DE-52 column. The column was washed, and the peak DNA polymerase was eluted using a 100–600 mM KCl linear gradient in Buffer A, concentrated in Buffer A containing 50%(w/v) PEG-6000, dialyzed in Buffer A containing 100 mM KCl;

(H) The solution was then applied to Heparin-Sepharose CL-4B column. The peak DNA polymerase was eluted with a linear gradient of 100–800 mM KCl in Buffer A, concentrated and finally dialyzed in buffer A containg 50% glycerol.

The resulting modified Bst DNA polymerase has been proved to be homogenous by polyacrylamide gel electrophoresis. And the enzyme obtained was stored in –20° C.

EXAMPLE 5

Determination of the thermostability of unmodified Bst DNA polymerase and modified Bst DNA polymerase The DNA polymerases of Examples 1 and 5 were incubated at 65° C. for 0, 5, 10, 20, 30, 40, 50 minutes respectively, and placed into ice-water immediately. The polymerase activity of these DNA polymerases was determined at 60° C.

The polymerase activity of DNA polymerase was determined as follows:

| 5 × Reaction Solution: | |
|---|---|
| 1M Tris-HCl (pH7.6) | 16.75 ml |
| 1M $MgCl_2$ | 1.675 ml |
| 1M β-Mercaptoethanol | 0.25 ml |
| $ddH_2O$ | adjusted to 50 ml |
| Reaction Storage: | |
| 5 × Reaction Solution | 60 μl |
| dNTPs (1 mM each) | 10 μl |
| 1.5 μg/μl DNase I activated calf thymus DNA | 10 μl |
| $ddH_2O$ | 10 μl |
| α-$^{32}$P-dATP | appropriate amt. |
| Reaction Mixture: | |
| Reaction Storage | 30 μl |
| Sample | 5 μl |
| $ddH_2O$ | 65 μl |

The reaction mixtures were prepared as per the recipe above, and incubated at 60° C. for 30 minutes. Then the reaction mixtures were pipetted onto DE-81 filters respectively. After all of the fluid has evaporated, the amount of radioactivity on each filter was measured with scintillation ($X_1$). The filters were washed three times with 0.3M $Na_2HPO_4$ at room temperature, 10 minutes each times, dried at room temperature and then the amount of radioactivity on each filter was measured again ($X_2$).

The polymerase activity of sample (u/ml)=

$$\left[\frac{X_2}{X_1} - \frac{X_{20}}{X_{10}}\right] \times 266$$

($X_{10}$ and $X_{20}$ are the amount of radioactivity measured with water as control sample)

Unit definition of polymerase activity: One unit is the amount of DNA polymerase required to incorporate 10 nanomoles of dNTPs into DNA in 30 minutes at 60° C.

Figure 1:
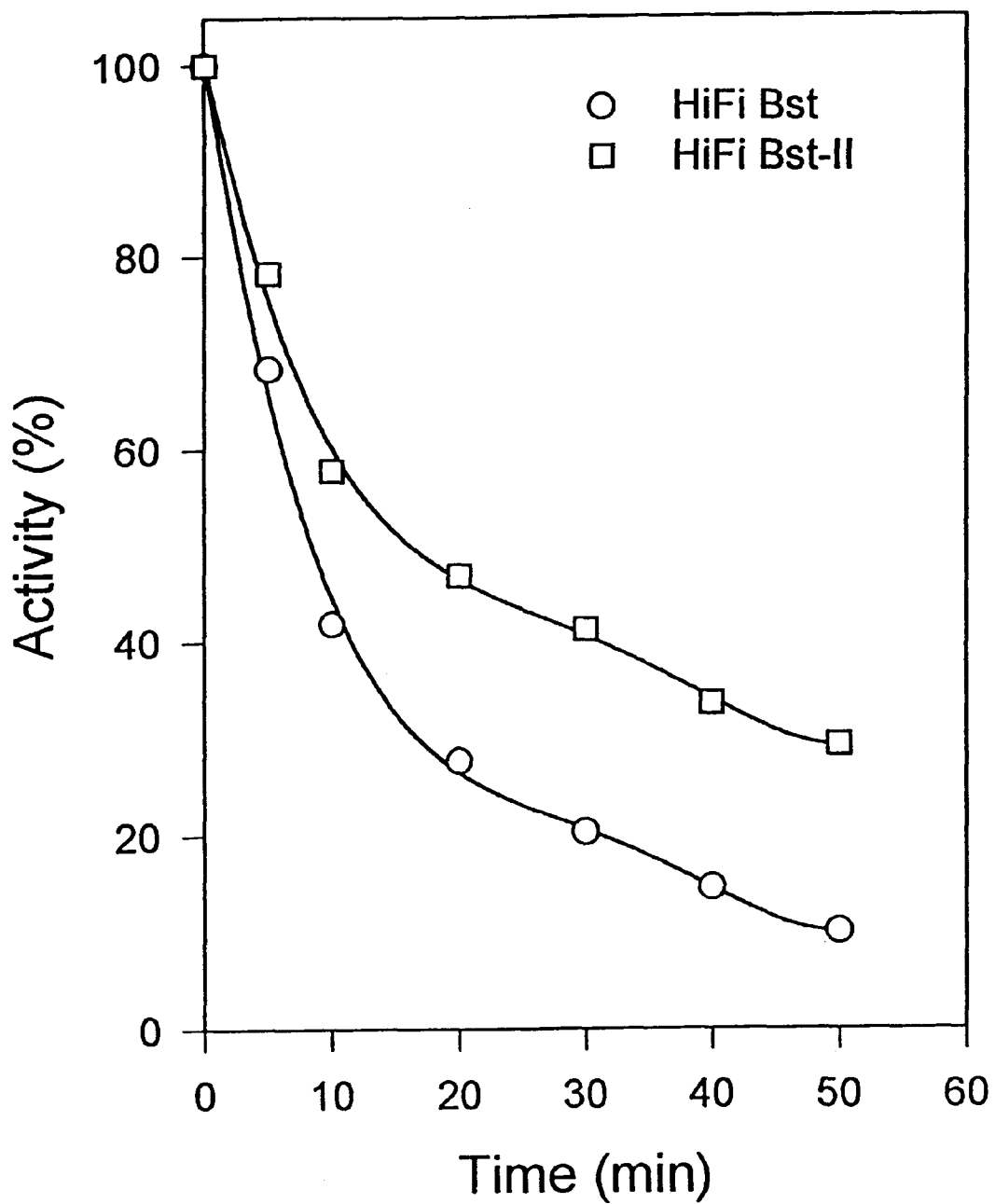
FIG. 1. This graph shows the thermostability at 65° C. of HIFI Bst-II and HiFI Bst.

The thermostability of DNA polymerase is expressed with the half life of polymerase activity at 65° C. FIG. 1 shows the comparison of thermostabilty of HiFi Bst and HiFi Bst-II. The half life of HiFi Bst at 65° C. was 8.5 minutes, and that of HiFi Bst-II was 16 minutes. HiFi Bst-II was more thermostable than HiFi Bst.

EXAMPLE 6

Demonstration of increased ddNTP incorporation by modified Bst DNA polymerase in suboptimal sequencing conditions The following procedure was followed:

1. The –20M13 forward primer was radiolabelled using γ-$^{32}$P-ATP and T4 Polynucleotide kinase;

2. The following components were combined in a microcentrifuge tube:

| | |
|---|---|
| 5 × Reaction Buffer | 2.0 μl |
| radiolabeled primer | 1.0 μl (2.5 ng) |
| Template | 7.0 μl (1 μg M13mp18 ssDNA) |

The final volume was 10 μl. The contents were mixed and spun for 2–3 seconds;

3. The tube were placed in a 75° C. water bath for 5 minutes. Then the tube was allowed to cool slowly to ambient temperature over a course of 10 minutes;

4. 1.0 μl of modified Bst DNA polymerase (of Example 5) (1u/μl) was added. The mixture was mixed gently and spun for 2–3 seconds;

5. 4 tubes were labelled "A", "C", "G", "T", respectively and 2 μl of each premixed nucleotide solution and 2.5 μl of main mixture (from step 3) was added to the respective reaction tube;

6. The tubes were incubated at 65° C. for 15 minutes;

7. The reactions were stopped by adding 4.0 μl of Stop Solution(95% deionized formamide, 10 mM EDTA, 0.05% xylene cyanol FF, 0.05% bromophenol blue) to each tube;

8. The samples were denatured at 90° C. for 2 minutes, and immediately placed on ice;

9. 4–5 μl of samples were loaded onto each lane of 6% (8 M urea) sequencing gel, and electrophoresis was carried out.

Note: The Components of the Premixed Nucleotide Solutions:

A mix: dNTPs 120 μM, ddATP 40 μM

C mix: dNTPs 120 μM, ddCTP 40 μM

G mix: dNTPs 120 μM, ddGTP 40 μM

T mix: dNTPs 120 μM, ddTTP 40 μM

FIG. 2 shows the comparison of ddNTP incorporation of HiFi Bst-II DNA polymerase and HiFi Bst DNA polymerase. In this radiolabeling DNA sequencing experiment, high concentrations of nucleotides were used in the reaction mixture and the ddNTP/dNTP ratio was reduced to a level (⅓) that is lower than the optimal range for DNA sequencing. HiFi Bst-II is shown to have more effective ddNTP incorporation. The DNA synthesis was often terminated by ddNTP incorporation in the HiFi Bst-II mixture, and the result showed uniform bands with synthesized small or large DNA fragments. As a contrast, HiFi Bst had a lower ddNTP incorporation. The DNA synthesis by HiFi Bst was less terminated, and most of the synthesized products were the larger DNA fragments.

EXAMPLE 7

Preparation of Denatured Double-stranded DNA Template

The following procedure was carried out.
1. Double-stranded DNA (about 3–5 μg) was adjusted to a final volume of 10 μl with TE (10 mM Tris-HCl, 1 mM EDTA, pH8.0);
2. 10 μl of 0.4N NaOH, 0.4 mM EDTA, was added;
3. The mixture was incubated at 65° C. for 15 minutes;
4. 2 μl of 2M sodium acetate, pH4.5, and 55 μl cold ethanol was added, and the mixture was placed in ice-water bath for 5 minutes;
5. The mixture was spun in a microcentrifuge at 4° C., 12500 rpm for 5 minutes;
6. The supernatant was drawn off and the pellet was washed with 200 μl of 70% ethanol;
7. The pellet was dried under vacuum for 2–3 minutes, and the DNA was dissolved in appropriate solution.

EXAMPLE 8

DNA sequencing using unmodified Bst DNA polymerase/modified Bst DNA polymerase with radiolabeled DATP for single- or denatured double-stranded DNA template The following procedure was carried out.
1. The following components were combined in a labeled microcentrifuge tube:

| | |
|---|---|
| 5 × Reaction Buffer | 2.0 μl |
| Primer | 1.0 μl (2.5–5.0 ng) |
| Template | 7.0 μl (250–500 ng ss DNA or 1–3 μg denatured ds DNA) |

The final volume was 10 μl. The contents were mixed and spun for 2–3 seconds;
2. The tube were placed in a 75° C. water bath for 5 minutes. Then the tubes were allowed to cool slowly to ambient temperature over a course of 10 minutes; (Note: Step 2 is optional for single-stranded template, and may be omitted at appropriate.)
3. 1.0 μl of HiFi Bst/HiFi Bst-II (1u/μl) and 1.0 μl of [α-$^{32}$P]dATP was added, and the mixture was mixed gently and spun for 2–3 seconds;
4. 4 tubes "A", "C", "G", "T" were labelled, and 2 μl of each premixed nucleotide solution and 2.5 μl of main mixture (from step 3) was added to the respective reaction tube;
5. The tubes were incubated at 65° C. for 2 minutes;
6. 2.0 μl of 0.5 mM dNTPs was added to each tube, and the tubes were mixed gently, spun for 2–3 seconds, and incubated at 65° C. for 2 minutes;
7. The reactions were stopped by adding 4.0 μl of Stop Solution(95% deionized formamide, 10 mM EDTA, 0.05% xylene cyanol FF, 0.05% bromophenol blue) to each tube;
8. The samples were denatured at 90° C. for 2 minutes, and immediately placed on ice;
9. 2–3 μl of the samples were loaded onto each lane of 6% (8M urea) sequencing gel, and electrophoresis was carried out.

Note: The Components of the Premixed Nucleotide Solutions for HiFi Bst:

A mix: dATP0.62 μM, dCTP 62 μM, dGTP 62 μM, dTTP 62 μM, ddATP 25 μM;

C mix: dATP 0.8 μM, dCTP 8 μM, dGTP 80 μM, dTTP 80 μM, ddCTP 50 μM;

G mix: dATP 0.8 μM, dCTP 80 μM, dGTP 4 μM, dTTP 80 μM, ddGTP 75 μM;

T mix: dATP 0.8 μM, dCTP 80 μM, dGTP 80 μM, dTTP 8 μM, ddTTP 150 μM.

The Components of the Premixed Nucleotide Solutions for HiFi Bst-II:

A mix: DATP 0.8 μM, dCTP 80 μM, dGTP 80 μM, dTTP 80 μM, ddATP 25 μM;

C mix: DATP 0.8 μM, dCTP 8 μM, dGTP 80 μM, dTTP 80 μM, ddCTP 20 μM;

G mix: DATP 0.8 μM, dCTP 80 μM, dGTP 8 μM, dTTP 80 μM, ddGTP 50 μM;

T mix: dATP 0.8 μM, dCTP 80 μM, dGTP 80 μM, dTTP 8 μM, ddTTP 50 μM.

FIG. 3 shows the comparison of radiolabeled DNA sequencing with HiFi Bst and HiFi Bst-II in their respective optimized reaction mixtures. The bands on a DNA sequencing gel with HiFi Bst-II were more uniform than those with HiFi Bst. The sequence pattern using HiFi Bst-II was better than that using HiFi Bst. This made the gel with HiFi Bst-II even easier to read. Moreover, the ratio of dideoxynucleotide concentration to deoxy-nucleotide concentration in Premixed Nucleotide Solutions for HiFi Bst-II was lower than that for HiFi Bst. For instance, the ddATP/dATP, ddCTP/dCTP, ddGTP/dGTP and ddTTP/dTTP ratios were 40, 6.25, 18.75 and 18.75, respectively, for HiFi Bst. The corresponding ratios for HiFi Bst-II were 40, 2.5, 6.25 and 6.25, respectively. Therefore, the concentrations of ddNTPs used in the termination reaction are reduced to about three-folds after HiFi Bst has been genetically modified.

EXAMPLE 9

DNA sequencing using unmodified Bst DNA polymerase/modified Bst DNA polymerase with dye-primers for single- or denatured double-stranded DNA template The following procedure was carried out.
1. The following was combined: 4.0 μl DNA template (300–600 ng for ssDNA or 1–2 μg denatured ds DNA) with 5.0 μl 5×Reaction Buffer. The mixture was mixed and spun for 2–3 seconds in a microcentrifuge;

2. 4 tubes were labeled "A", "C", "G", "T" and the pre-mixed DATP, dCTP, dGTP, dTTP reagents were added to each reaction tube:

|  | Reaction tube | | | |
| --- | --- | --- | --- | --- |
|  | A | C | G | T |
| A-REG primer (0.2 uM) | 1.0 ul |  |  |  |
| C-FAM primer (0.2 uM) |  | 1.0 ul |  |  |
| G-TMR primer (0.4 uM) |  |  | 1.0 ul |  |
| T-ROX primer (0.4 uM) |  |  |  | 1.0 ul |
| A terminator mix | 2.0 ul |  |  |  |
| C terminator mix |  | 2.0 ul |  |  |
| G terminator mix |  |  | 2.0 ul |  |
| T terminator mix |  |  |  | 2.0 ul |
| 5 × Reaction buffer with DNA template | 2.0 ul | 2.0 ul | 2.0 ul | 2.0 ul |
| Total volume | 5.0 ul | 5.0 ul | 5.0 ul | 5.0 ul |

3. The tubes were placed in 75° C. bath for 5 minutes, and allowed to cool slowly to ambient temperature over the course of 10 minutes;

(Note: Step 3 is optional for single-stranded template, and may be omitted as appropriate.)

4. 1 $\mu$l of HiFi Bst/HiFi Bst-II (0.5u/$\mu$l) was added to each tube, and the tubes were spun for 2–3 seconds;

5. The tubes were incubated at 65° C. for 5 minutes;

6. The contents of the "A", "C", "G" and "T" tubes were pooled, and 1.5 $\mu$l of 7.5M ammonium acetate and 55 $\mu$l of ethanol was added. The mixtured was mixed in a vortex and then placed on ice for 20 minutes;

7. The mixture was centrifuged at 12,500 rpm for 20 minutes at 4° C.;

8. The supernatant was drawn off, and the pellet was washed with 200 $\mu$l of 70% ethanol;

9. The pellet was vacuum dried for 2–3 minutes, and resuspended in 4 $\mu$l of loading buffer (5:1 deionized formamide: 25 mM EDTA with 50 mg/ml Blue Dextran);

10. The sample was heated at 75° C. for 2–3 minutes, and immediately placed on ice;

11. 2–3 $\mu$l of sample was loaded onto a lane of the 4% (6M urea) sequencing gel, and ABI PRISM™ 377 DNA Sequencer (from Perkin Elmer) was used to collect data.

Note: Dye primer: DYEnamic Energy Transfer Dye Primers (from Amersham): −21 M13 forward: 5'-FAM-S$^Y$SSSSSTGT*AAAACGACGGCCAGT-3' (SEQ ID NO:11) YS=1'2'-dideoxyribose T*=T attached with Dye 2(A-REG, C-FAM, G-TMR, T-ROX)

Figure 4B:
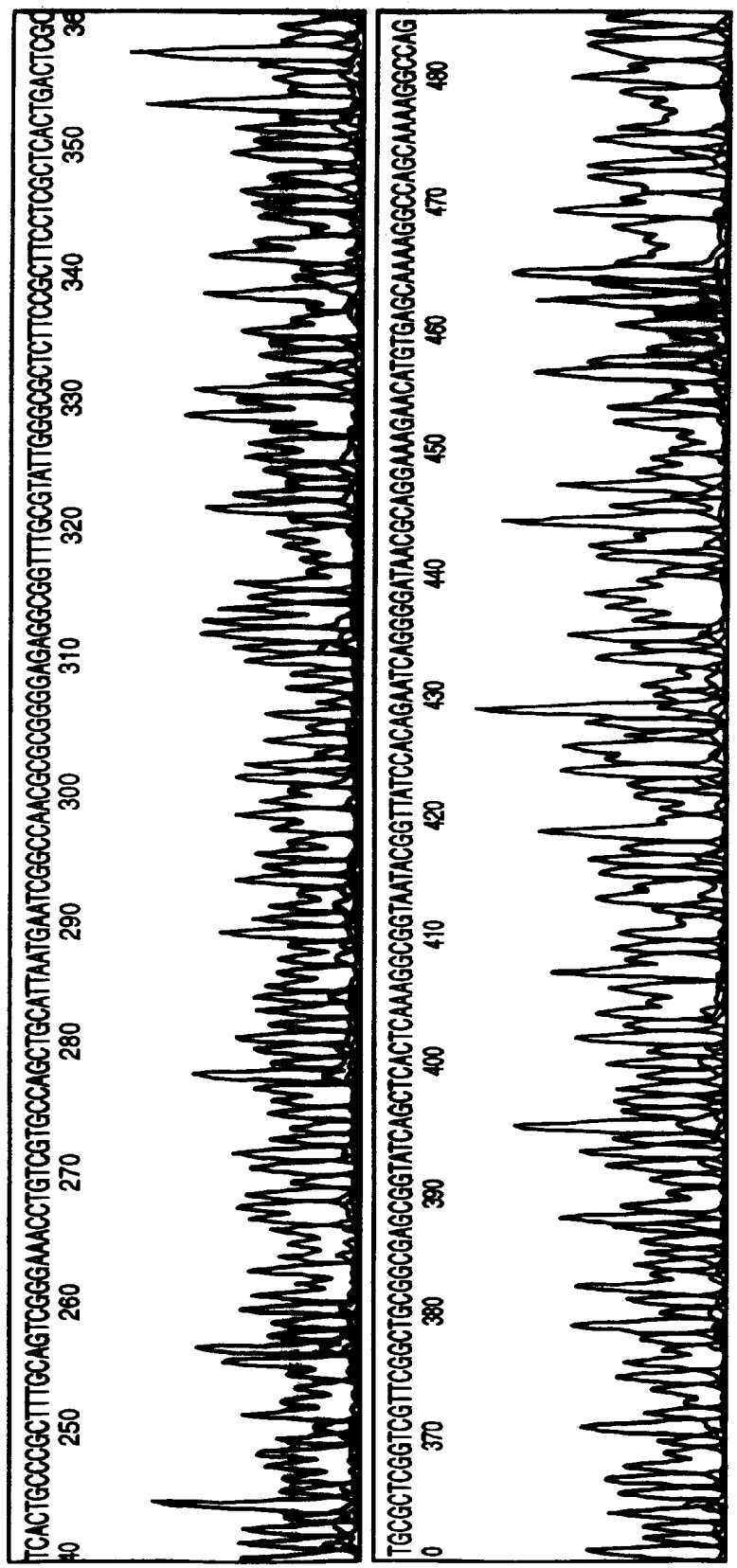
Figure 4C:
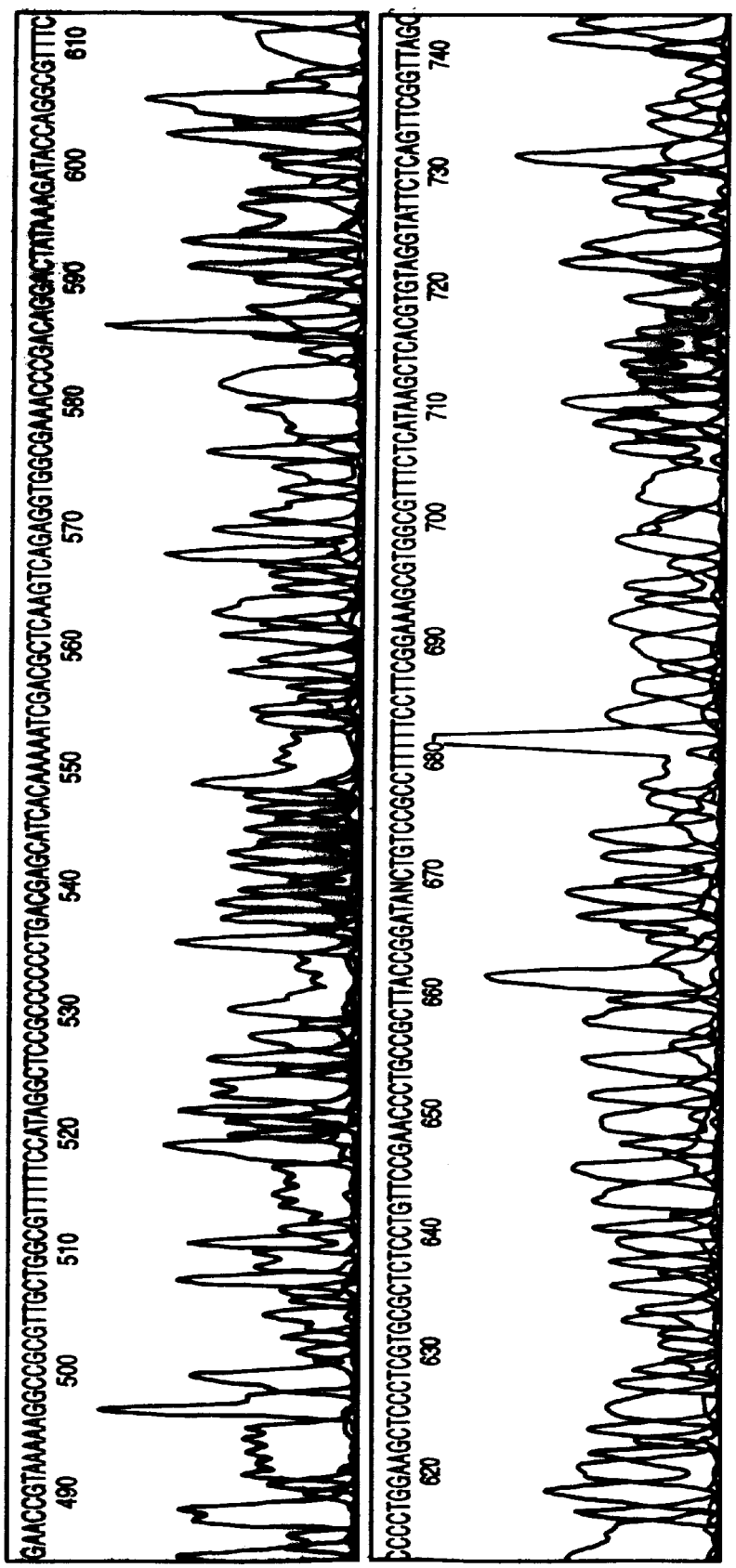
Figure 5B:
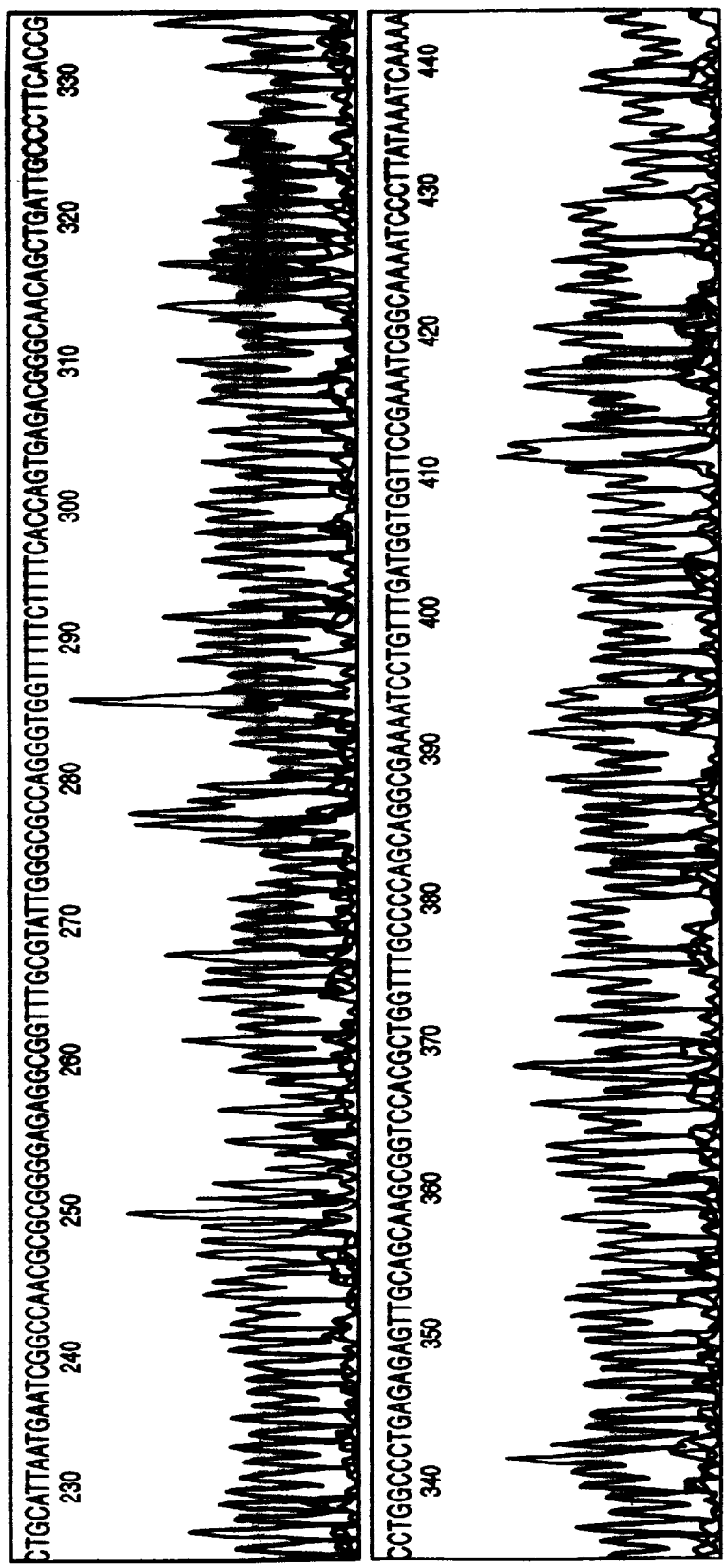
Figure 5C:
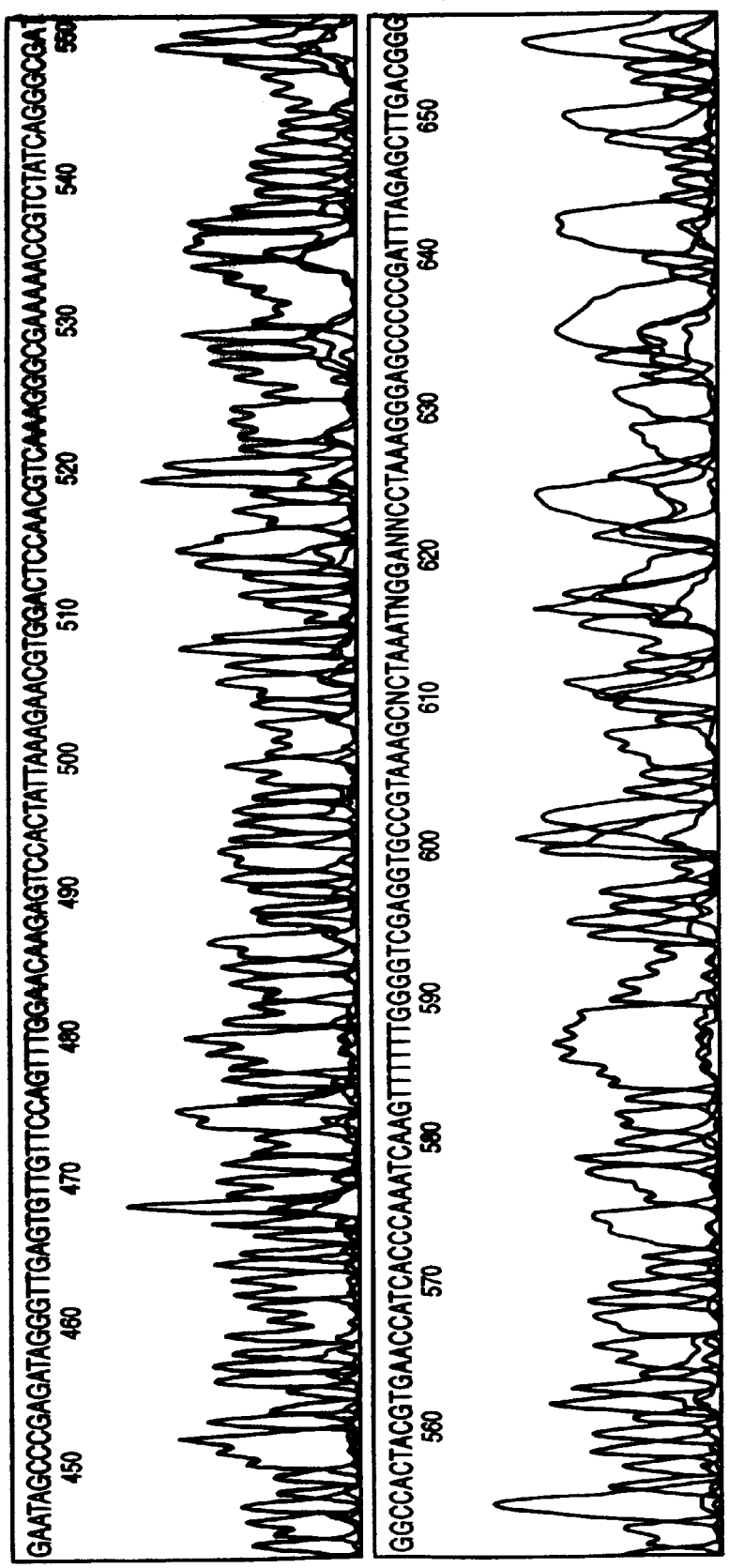

FIG. 4 and FIG. 5 show the results of dye-primer DNA sequencing with HiFi Bst and HiFi Bst-II. Both DNA polymerases generated similar sequencing results although the peaks on the color plot by HiFi Bst II appear to be more even in height.

EXAMPLE 10

DNA sequencing using unmodified Bst DNA polymerase/modified Bst DNA polymerase with dye-terminators for single- or denatured double-stranded DNA template The following procedure was carried out.

1. The following components were combined in a labeled microcentrifuge tube:

| 5 × Reaction Buffer | 4.0 $\mu$l |
| --- | --- |
| Template | 8.0 $\mu$l (2–3 $\mu$g ss DNA or 4–6 $\mu$g denatured ds DNA) |
| Primer | 2.0 $\mu$l (5–10 ng) |

The final volume was 14 $\mu$l. The contents were mixed and spun for 2–3 seconds;

2. The tube was placed in a 75° C. water bath for 5 minutes;

3. The cube was allowed to cool slowly to ambient temperature over a course of 10 minutes;

(Note: Steps 2 and 3 are optional for single-stranded template, and may be omitted as appropriate.)

4. 1.0 $\mu$l of HiFi Bst/HiFi Bst-II (1–2u/$\mu$l), 5 $\mu$l of nucleotides premix (containing Perkin Elmer-ABI fluorescent dye-labeled nucleotide terminators), were added and the tube was spun for 2–3 seconds;

5. The mixture was incubated at 65° C. for 10 minutes;

6. 80 $\mu$l of H$_2$O was added to the reaction mix, and the dye terminators were extracted with 100 $\mu$l of phenol:H$_2$O:chloroform (68:18:14) reagent twice. The sample was vortexed and centrifuged, and the aqueous upper layer was transferred to a clean tube;

7. To the tube was added 15 $\mu$l of 2M sodium acetate, pH 4.5, and 300 $\mu$l of ethanol, and the tube was vortexed and placed in ice-water bath for 20 minutes;

8. The tube was centrifuged with 12,500 rpm for 20 minutes at 4° C.;

9. The supernatant was drawn off, and the pellet was washed with 200 $\mu$l of 70% ethanol;

10. The pellet was vacuum dried for 2–3 minutes, and resuspended in 4 $\mu$l of loading buffer (5:1 deionized formamide: 25 mM EDTA with 50 mg/ml Blue Dextran);

11. The sample was heated at 90° C. for 2–3 minutes, and immediately placed on ice;

12. 2–3 $\mu$l of sample was loaded onto a lane of the 4% (6M urea) sequencing gel, and ABI PRISM™ 377 DNA Sequencer (from Perkin Elmer) was employed to collect data, using appropriate amounts of nucleotide pre-mixed reagents.

Figure 6B:
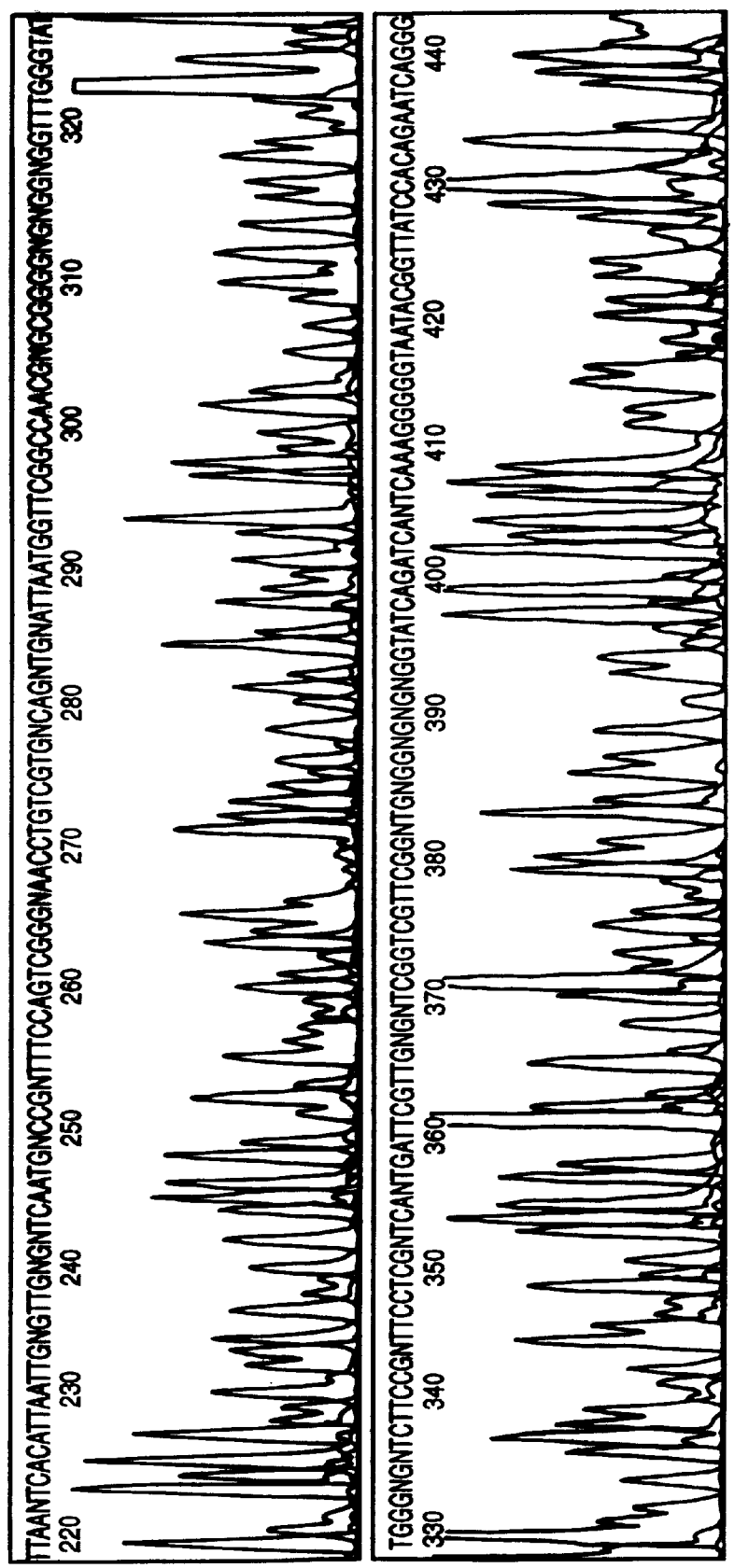
Figure 6C:
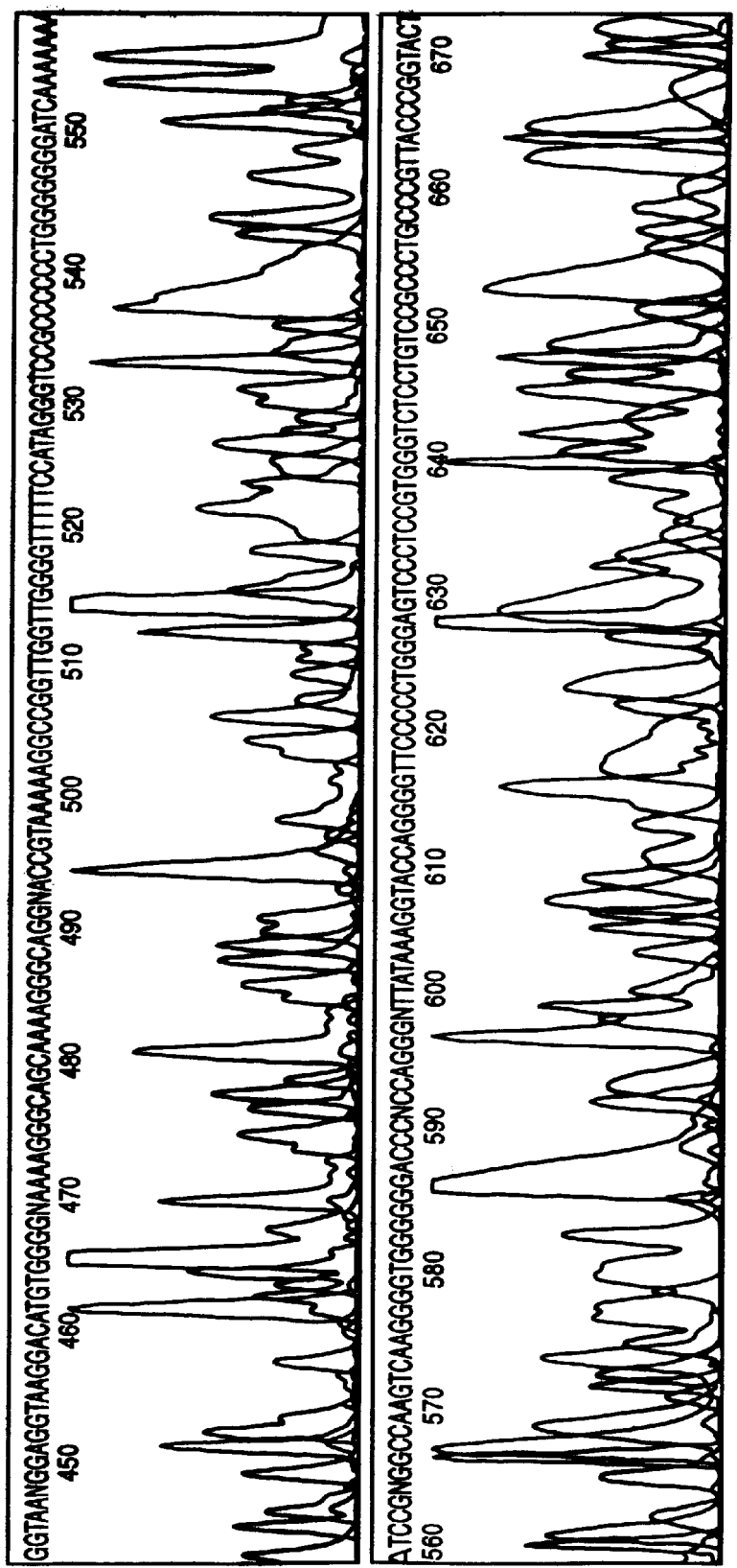
Figure 7B:
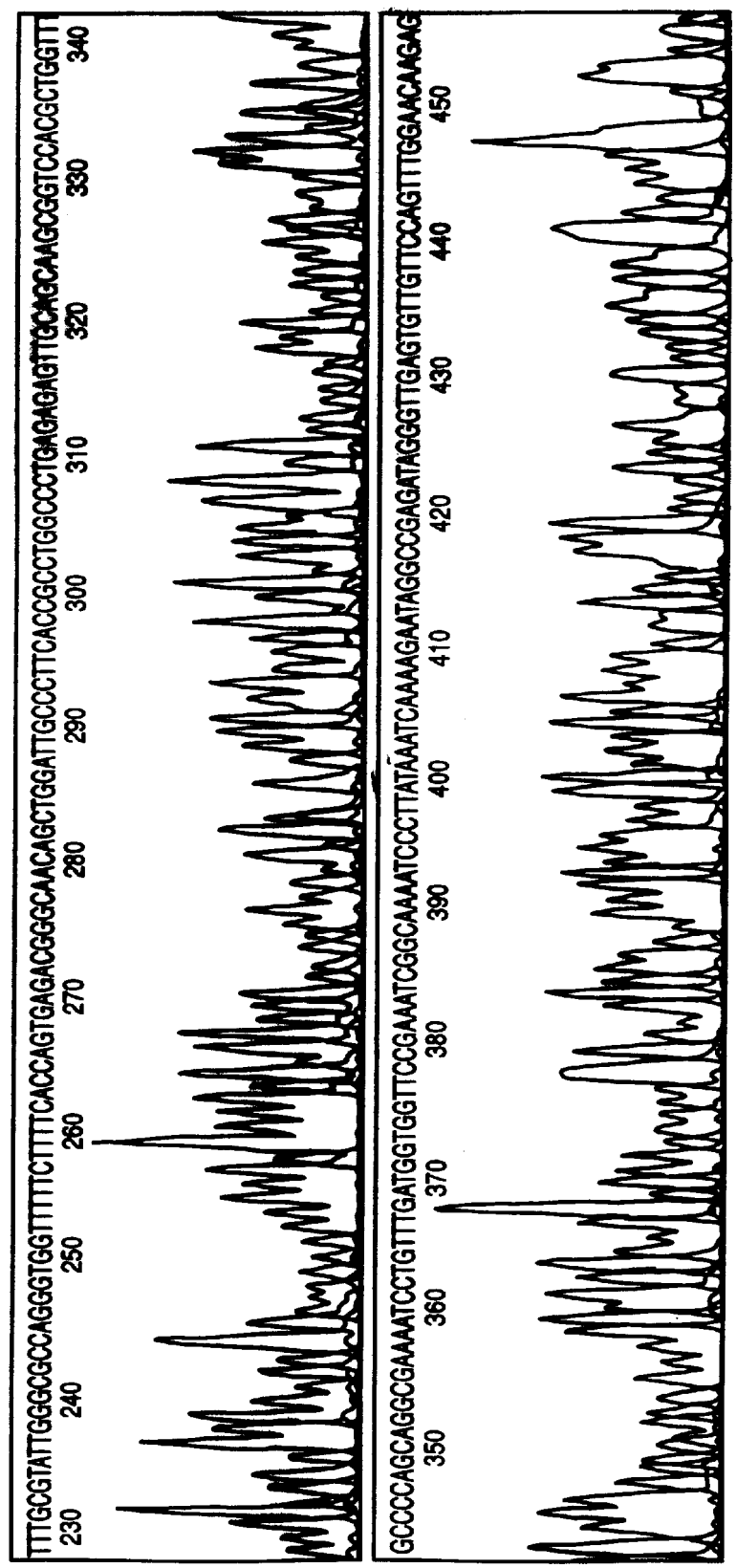
Figure 7C:
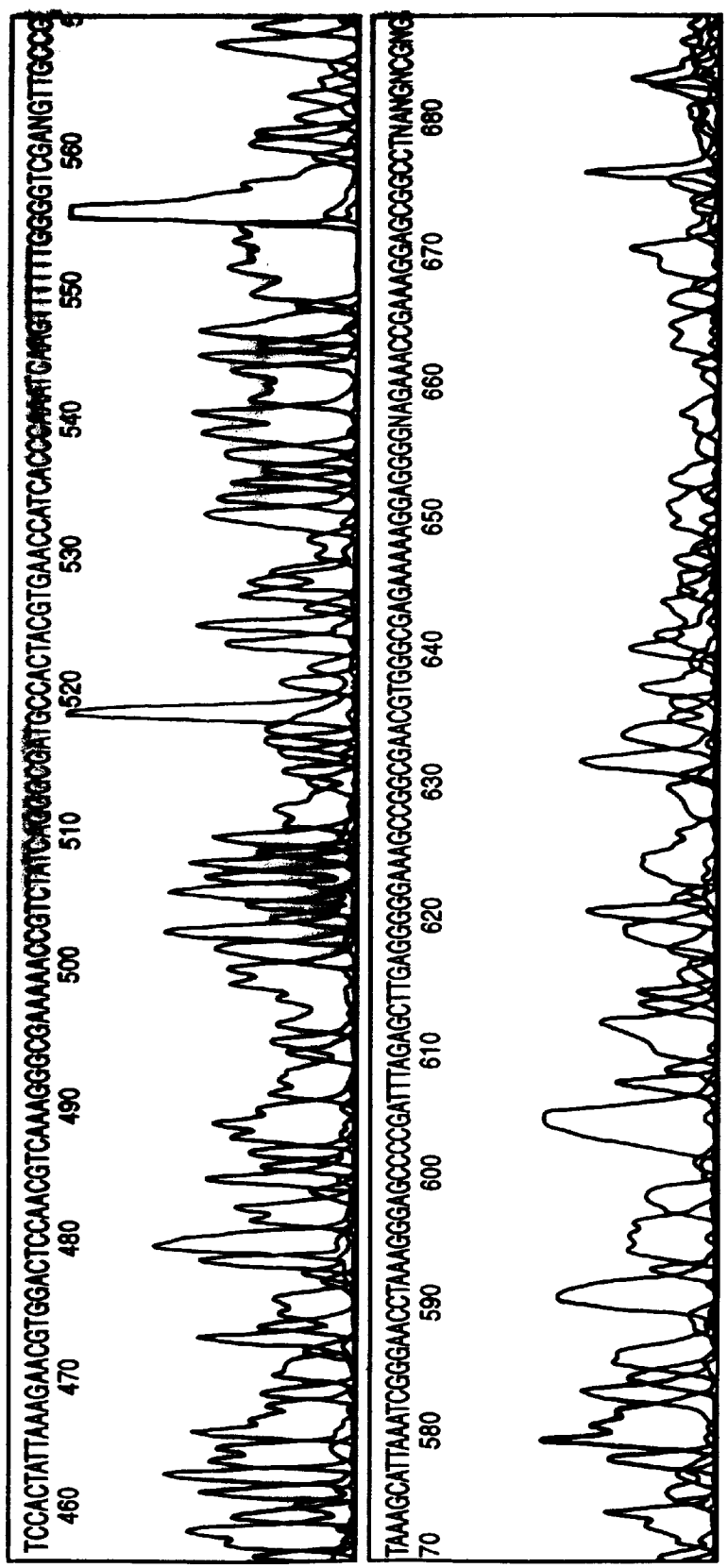

FIG. 6 and FIG. 7 show the results of dye-terminator DNA sequencing with HiFi Bst and HiFi Bst-II. There was data lost in dye-terminator DNA sequencing with HiFi Bst, especially the "C" after "G" or "A" and "A" after "G". In FIG. 8, corrections of the missing or ambiguous bases, according to the known pGEM sequence, have been indicated below the letters "N" or below the incorrect base letters. This problem caused ambiguity in DNA sequencing. But it was resolved in dye-terminator DNA sequencing with the modified Bst DNA polymerase of this invention.

REFERENCES

1. Sanger, F., Nicklen, S. & Coulson, A. R. Proc. Nat. Acad. Sci., USA 74: 5463–5467. 1977.
2. CURRENT PROTOCOLS IN MOLECULAR BIOLOGY, Ausubel, F. M. et. Al. (Editors) Vol. I., John Wiley & Sons, Inc. 1995. pp 7.4.17–7.4.24.
3. Ibid p. 7.4.31.
4. Ye, S. Y. & Hong, G. F., Scientia Sinica (Series B) 30: 503–506. 1987.
5. In Ref. 2, p. 7.4.18 Table 7.4.2.

6. EPICENTRE TECHNOLOGIES CATALOG, 1994/95 Products for Molecular & Cellular Biology, Page 1, "What's new in this catalog?"
7. Okazaki, T. & Kornberg, A. J. Biol. Chem. 239: 259–268. 1964.
8. Jacobsen, H., Klenow, H. & Overgard-Hansen, K. Eur. J. Biochem. 45: 623–627. 1974.
9. McClary, J., Ye, s. Y., Hong, G. F. & Witney, F. DNA Sequence 1: 173–180. 1991.
10. Mead, D. A., McClary, J. A., Luckey, J. A., et Al. BioTechniques 11: 76–87. 1991.
11. Earley, J. J., Kuivaniemi, H. Prockop, D. J. & Tromp, G. BioTechniques 17: 156–165,1994.
12. Mardis, E. R. & Bruce, A. R. BioTechniques 7: 840–850. 1989.
13. Chissoe, S. L. et al., Methods: A Companion to Methods in Enzymology, 3, 555–65, 1991
14. Kunkel, T. A. et al., Methods Enzymol. 154:367–382, 1987

All references mentioned herein are incorporated in their entirety by reference.

What is claimed is:

1. A modified DNA polymerase which during DNA sequencing effectively incorporates fluorescent dye-labeled dideoxynucleotide terminators ddCTP, ddATP, ddTTP and ddGTP, and their analogs, and reduces selective discrimination against incorporation of fluorescent dye-labeled dideoxynucleotide terminators ddCTP and ddATP, wherein the DNA polymerase in its unmodified state selectively discriminates against incorporation of fluorescent dye-labeled dideoxynucleotide terminators ddCTP and ddATP but does not discriminate against incorporation of fluorescent dye-labeled dideoxynucleotide terminators ddTTP and ddGTP.

2. The DNA polymerase according to claim 1 which is a modified Bacillus stearothermophilus DNA polymerase.

3. The DNA polymerase according to claim 1 which has an amino acid sequence that shares not less than 95% identity of a DNA polymerase isolated from a strain of Bacillus stearothermophilus, Bacillus caldotenax or Bacillus caldolyticus.

4. The DNA polymerase according to claim 1 wherein the DNA polymerase is a modified DNA polymerase obtained from a mesophilic bacterium.

5. The DNA polymerase according to claim 1 which is a thermostable DNA polymerase having proofreading 3'-5' exonuclease activity during DNA sequencing of a DNA strand from a template, such that the DNA polymerase functions to excise mismatched nucleotides from the 3' terminus of the DNA strand at a faster rate than the rate at which the DNA polymerase functions to remove nucleotides matched correctly with nucleotides of the template.

6. A modified Bacillus stearothermophilus DNA polymerase which during DNA sequencing effectively incorporates fluorescent dye-labeled dideoxynucleotide terminators ddCTP, ddATP, ddTTP and ddGTP, and reduces selective discrimination against incorporation of fluorescent dye-labeled dideoxynucleotide terminators ddCTP and ddATP, wherein the DNA polymerase in its unmodified state selectively discriminates against incorporation of fluorescent dye-labeled dideoxynucleotide terminators ddCTP and ddATP but does not discriminate against incorporation of fluorescent dye-labeled dideoxynucleotide terminators ddTTP and ddGTP, wherein the DNA polymerase has proofreading 3'-5' exonuclease activity during DNA sequencing of a DNA strand from a template, such that the DNA polymerase functions to excise mismatched nucleotides from the 3' terminus of the DNA strand at a faster rate at which the DNA polymerase functions to remove nucleotides matched correctly with nucleotides of the template.

7. The DNA polymerase according to claim 6, which has the amino acid sequence SEQ ID NO:4.

8. The DNA polymerase according to claim 6, which is encoded by a DNA segment having polymerase isolated from a strain of Bacillus stearothermophilus or Bacillus caldotenax, so that the modified nucleotide sequence encodes threonine, proline and leucine residues at positions 342–344, respectively, and a tyrosine residue at position 422.

9. A kit for direct DNA sequencing comprising the modified DNA polymerase of claim 1 and at least one fluorescent dye-labeled ddNTP.

10. The kit according to claim 9 wherein the modified DNA polymerase is a modified Bacillus stearothermophilus, Bacillus caldotenax or Bacillus caldolyticus DNA polymerase.

11. The kit according to claim 9 wherein the modified DNA polymerase has an amino acid sequence that shares not less than 95% identity of a DNA polymerase isolated from a strain of Bacillus stearothermophilus, Bacillus caldotenax or Bacillus caldolyticus.

12. The kit according to claim 9 wherein the modified DNA polymerase is modified DNA polymerase obtained from a mesophilic bacterium.

13. The kit according to claim 9 wherein the modified DNA polymerase has proofreading 3'-5' exonuclease activity during DNA sequencing of a DNA strand from a template, such that the DNA polymerase functions to excise mismatched nucleotides from the 3' terminus of the DNA strand at a faster rate than the rate at which the DNA polymerase functions to remove nucleotides matched correctly with nucleotides of the template.

14. The kit according to claim 9, wherein the modified DNA polymerase is modified Bacillus stearothermophilus DNA polymerase which has proofreading 3'-5' exonuclease activity during DNA sequencing of a DNA strand from a template, such that the DNA polymerase functions to excise mismatched nucleotides from the 3' terminus of the DNA strand at a faster rate than the rate at which the DNA polymerase functions to remove nucleotides matched correctly with nucleotides of the template.

15. The kit according to claim 9 wherein the modified DNA polymerase has the amino acid sequence SEQ ID NO:4.

16. The kit according to claim 9 wherein the modified DNA polymerase is encoded by a DNA segment having the nucleotide sequence of SEQ ID:NO 3.

* * * * *

SEQUENCE LISTING

<160> NUMBER OF SEQ ID NOS: 11

<210> SEQ ID NO 1
<211> LENGTH: 1764
<212> TYPE: DNA
<213> ORGANISM: Bacillus stearothermophilus

<400> SEQUENCE: 1

```
gccgaagggg agaaaccgct tgaggagatg gagtttgcca tcgttgacgt cattaccgaa   60
gagatgcttg ccgacaaggc agcgcttgtc gttgaggtga tggaagaaaa ctaccacgat  120
gccccgattg tcggaatcgc actagtgaac gagcatgggc gattttttat gcgcccggag  180
accgcgctgg ctgattcgca attttttagca tggcttgccg atgaaacgaa gaaaaaaagc  240
atgtttgacg ccaagcgggc agtcgttgcc ttaaagtgga aaggaattga gcttcgcggc  300
gtcgcctttg atttattgct cgctgcctat ttgctcaatc cggctcaaga tgccggcgat  360
atcgctgcgg tggcgaaaat gaaacaatat gaagcggtgc ggtcggatga agcggtctat  420
ggcaaaggcg tcaagcggtc gctgccggac gaacagacgc ttgctgagca tctcgttcgc  480
aaagcggcag ccatttgggc gcttgagcag ccgtttatgg acgatttgcg gaacaacgaa  540
caagatcaat tattaacgaa gcttgagcac gcgctggcgg cgattttggc tgaaatggaa  600
ttcactgggg tgaacgtgga tacaaagcgg cttgaacaga tgggttcgga gctcgccgaa  660
caactgcgtg ccatcgagca gcgcatttac gagctagccg gccaagagtt caacattaac  720
tcaccaaaac agctcggagt cattttattt gaaaagctgc agctaccggt gctgaagaag  780
acgaaaacag gctattcgac ttcggctgat gtgcttgaga agcttgcgcc gcatcatgaa  840
atcgtcgaaa acattttgca ttaccgccag cttggcaaac tgcaatcaac gtatattgaa  900
ggattgttga aagttgtgcg ccctgatacc ggcaaagtgc atacgatgtt caaccaagcg  960
ctgacgcaaa ctgggcggct cagctcggcc gagccgaact tgcaaaacat tccgattcgg 1020
ctcgaagagg ggcggaaaat ccgccaagcg ttcgtcccgt cagagccgga ctgctcatt  1080
ttcgccgccg attactcaca aattgaattg cgcgtcctcg cccatatcgc cgatgacgac 1140
aatctaattg aagcgttcca acgcgatttg gatattcaca caaaacggc gatggacatt 1200
ttccagttga gcgaagagga agtcacggcc aacatgcgcc gccaggcaaa ggccgttaac 1260
ttcggtatcg tttacggaat tagcgattac ggattggcgc aaaacttgaa cattacgcgc 1320
aaagaagctg ccgaatttat cgaacgttac ttcgccagct ttccgggcgt aaagcagtat 1380
atggaaaaca tagtgcaaga agcgaaacag aaaggatatg tgacaacgct gttgcatcgg 1440
cgccgctatt tgcctgatat tacaagccgc aatttcaacg tccgcagttt tgcagagcgg 1500
acggccatga acacgccaat tcaaggaagc gccgctgaca ttattaaaaa agcgatgatt 1560
gatttagcgg cacggctgaa agaagagcag cttcaggctc gtcttttgct gcaagtgcat 1620
gacgagctca ttttgaaagc gccaaaagag gaaattgagc gattatgtga gcttgttccg 1680
gaagtgatgg agcaggccgt tacgctccgc gtgccgctga aagtcgacta ccattacggc 1740
ccaacatggt atgatgccaa ataa                                         1764
```

<210> SEQ ID NO 2
<211> LENGTH: 587
<212> TYPE: PRT
<213> ORGANISM: Bacillus stearothermophilus

<400> SEQUENCE: 2

```
Ala Glu Gly Glu Lys Pro Leu Glu Glu Met Glu Phe Ala Ile Val Asp
  1               5                  10                  15
Val Ile Thr Glu Glu Met Leu Ala Asp Lys Ala Ala Leu Val Val Glu
             20                  25                  30
Val Met Glu Glu Asn Tyr His Asp Ala Pro Ile Val Gly Ile Ala Leu
         35                  40                  45
Val Asn Glu His Gly Arg Phe Phe Met Arg Pro Glu Thr Ala Leu Ala
     50                  55                  60
Asp Ser Gln Phe Leu Ala Trp Leu Ala Asp Glu Thr Lys Lys Lys Ser
 65                  70                  75                  80
Met Phe Asp Ala Lys Arg Ala Val Val Ala Leu Lys Trp Lys Gly Ile
                 85                  90                  95
Glu Leu Arg Gly Val Ala Phe Asp Leu Leu Leu Ala Ala Tyr Leu Leu
```

```
                100                 105                 110
    Asn Pro Ala Gln Asp Ala Gly Asp Ile Ala Ala Val Ala Lys Met Lys
                    115                 120                 125
    Gln Tyr Glu Ala Val Arg Ser Asp Glu Ala Val Tyr Gly Lys Gly Val
                130                 135                 140
    Lys Arg Ser Leu Pro Asp Glu Gln Thr Leu Ala Glu His Leu Val Arg
145                 150                 155                 160
    Lys Ala Ala Ile Trp Ala Leu Glu Gln Pro Phe Met Asp Asp Leu
                    165                 170                 175
    Arg Asn Asn Glu Gln Asp Gln Leu Leu Thr Lys Leu Glu His Ala Leu
                180                 185                 190
    Ala Ala Ile Leu Ala Glu Met Glu Phe Thr Gly Val Asn Val Asp Thr
                195                 200                 205
    Lys Arg Leu Glu Gln Met Gly Ser Glu Leu Ala Glu Gln Leu Arg Ala
                210                 215                 220
    Ile Glu Gln Arg Ile Tyr Glu Leu Ala Gly Gln Glu Phe Asn Ile Asn
225                 230                 235                 240
    Ser Pro Lys Gln Leu Gly Val Ile Leu Phe Glu Lys Leu Gln Leu Pro
                    245                 250                 255
    Val Leu Lys Lys Thr Lys Thr Gly Tyr Ser Thr Ser Ala Asp Val Leu
                260                 265                 270
    Glu Lys Leu Ala Pro His His Glu Ile Val Glu Asn Ile Leu His Tyr
                275                 280                 285
    Arg Gln Leu Gly Lys Leu Gln Ser Thr Tyr Ile Glu Gly Leu Leu Lys
                290                 295                 300
    Val Val Arg Pro Asp Thr Gly Lys Val His Thr Met Phe Asn Gln Ala
305                 310                 315                 320
    Leu Thr Gln Thr Gly Arg Leu Ser Ser Ala Glu Pro Asn Leu Gln Asn
                    325                 330                 335
    Ile Pro Ile Arg Leu Glu Glu Gly Arg Lys Ile Arg Gln Ala Phe Val
                340                 345                 350
    Pro Ser Glu Pro Asp Trp Leu Ile Phe Ala Ala Asp Tyr Ser Gln Ile
                355                 360                 365
    Glu Leu Arg Val Leu Ala His Ile Ala Asp Asp Asn Leu Ile Glu
                370                 375                 380
    Ala Phe Gln Arg Asp Leu Asp Ile His Thr Lys Thr Ala Met Asp Ile
385                 390                 395                 400
    Phe Gln Leu Ser Glu Glu Val Thr Ala Asn Met Arg Arg Gln Ala
                    405                 410                 415
    Lys Ala Val Asn Phe Gly Ile Val Tyr Gly Ile Ser Asp Tyr Gly Leu
                420                 425                 430
    Ala Gln Asn Leu Asn Ile Thr Arg Lys Glu Ala Ala Glu Phe Ile Glu
                435                 440                 445
    Arg Tyr Phe Ala Ser Phe Pro Gly Val Lys Gln Tyr Met Glu Asn Ile
                450                 455                 460
    Val Gln Glu Ala Lys Gln Lys Gly Tyr Val Thr Thr Leu Leu His Arg
465                 470                 475                 480
    Arg Arg Tyr Leu Pro Asp Ile Thr Ser Arg Asn Phe Asn Val Arg Ser
                    485                 490                 495
    Phe Ala Glu Arg Thr Ala Met Asn Thr Pro Ile Gln Gly Ser Ala Ala
                500                 505                 510
    Asp Ile Ile Lys Lys Ala Met Ile Asp Leu Ala Ala Arg Leu Lys Glu
                515                 520                 525
    Glu Gln Leu Gln Ala Arg Leu Leu Leu Gln Val His Asp Glu Leu Ile
                530                 535                 540
    Leu Glu Ala Pro Lys Glu Glu Ile Glu Arg Leu Cys Glu Leu Val Pro
545                 550                 555                 560
    Glu Val Met Glu Gln Ala Val Thr Leu Arg Val Pro Leu Lys Val Asp
                    565                 570                 575
    Tyr His Tyr Gly Pro Thr Trp Tyr Asp Ala Lys
                580                 585
```

<210> SEQ ID NO 3
<211> LENGTH: 1764
<212> TYPE: DNA
<213> ORGANISM: Bacillus stearothermophilus

<400> SEQUENCE: 3

```
    atggccgaag gggagaaacc gcttgaggag atggagtttg ccatcgttga cgtcattacc   60
    gaagagatgc ttgccgacaa ggcagcgctt gtcgttgagg tgatggaaga aaactaccac  120
    gatgccccga ttgtcggaat cgcactagtg aacgagcatg gcgatttttt tatgcgcccg  180
    gagaccgcgc tggctgattc gcaatttttta gcatggcttg ccgatgaaac gaagaaaaaa  240
    agcatgtttg acgccaagcg ggcagtcgtt gccttaaagt ggaaaggaat tgagcttcgc  300
    ggcgtcgcct ttgatttatt gctcgctgcc tatttgctca atccggctca agatgccggc  360
    gatatcgctg cggtggcgaa aatgaaacaa tatgaagcgg tcgtcggga tgaagcggtc  420
    tatggcaaag gcgtcaagcg gtcgctgccg gacgaacaga cgcttgctga gcatctcgtt  480
    cgcaaagcgg cagccatttg ggcgcttgag cagccgttta tggacgattt gcggaacaac  540
```

-continued

```
gaacaagatc aattattaac gaagcttgag cacgcgctgg cggcgatttt ggctgaaatg  600
gaattcactg gggtgaacgt ggatacaaag cggcttgaac agatgggttc ggagctcgcc  660
gaacaactgc gtgccatcga gcagcgcatt tacgagctgg ccggccaaga gttcaacatt  720
aactcaccaa aacagctcgg agtcatttta tttgaaaagc tgcagctacc ggtgctgaag  780
aagacgaaaa caggctattc gacttcggct gatgtgcttg agaagcttgc gccgcatcat  840
gaaatcgtcg aaaacatttt gcattaccgc cagcttggca aactgcaatc aacgtatatt  900
gaaggattgt tgaaagttgt gcgccctgat accggcaaag tgcatacgat gttcaaccaa  960
gcgctgacgc aaactggggc gctcagctcg gccgagccga acttgcaaaa cattccgatt 1020
cggaccccac tggggcggaa aatccgccaa gcgttcgtcc cgtcagagcg ggactggctc 1080
atttttcgccg ccgattactc acaaattgaa ttgcgcgtcc tcgcccatat cgccgatgac 1140
gacaatctaa ttgaagcgtt ccaacgcgat ttggatattc acacaaaaac ggcgatggac 1200
atttttccagt tgagcgaaga ggaagtcacg gccaacatgc gccgccaggc aaaggccgtt 1260
aactacggta tcgtttacgg aattagcgat tacggattgg cgcaaaactt gaacattacg 1320
cgcaaagaag ctgccgaatt tatcgaacgt tacttcgcca gctttccggg cgtaaagcag 1380
tatatgggaaa acatagtgca agaagcgaaa cagaaaggat atgtgacaac gctgttgcat 1440
cggcgccgct atttgcctga tattacaagc cgcaatttca acgtccgcag ttttgcagag 1500
cggacggcca tgaacacgcc aattcaagga agcgccgctg acattattaa aaaagcgatg 1560
attgatttag cggcacggct gaaagaagag cagcttcagg ctcgtctttt gctgcaagtg 1620
catgacgagc tcattttgga agcgccaaaa gaggaaattg agcgattatg tgagcttgtt 1680
ccggaagtga tggagcaggc cgttacgctc cgcgtgccgc tgaaagtcga ctaccattac 1740
ggcccaacat ggtatgatgc caaa                                         1764
```

<210> SEQ ID NO 4
<211> LENGTH: 588
<212> TYPE: PRT
<213> ORGANISM: Bacillus stearothermophilus

<400> SEQUENCE: 4

```
Met Ala Glu Gly Glu Lys Pro Leu Glu Glu Met Glu Phe Ala Ile Val
 1               5                  10                  15
Asp Val Ile Thr Glu Glu Met Leu Ala Asp Lys Ala Ala Leu Val Val
            20                  25                  30
Glu Val Met Glu Glu Asn Tyr His Asp Ala Pro Ile Val Gly Ile Ala
        35                  40                  45
Leu Val Asn Glu His Gly Arg Phe Phe Met Arg Pro Glu Thr Ala Leu
    50                  55                  60
Ala Asp Ser Gln Phe Leu Ala Trp Leu Ala Asp Glu Thr Lys Lys Lys
65                  70                  75                  80
Ser Met Phe Asp Ala Lys Arg Ala Val Val Ala Leu Lys Trp Lys Gly
                85                  90                  95
Ile Glu Leu Arg Gly Val Ala Phe Asp Leu Leu Ala Ala Tyr Leu
            100                 105                 110
Leu Asn Pro Ala Gln Asp Ala Gly Asp Ile Ala Val Ala Lys Met
        115                 120                 125
Lys Gln Tyr Glu Ala Val Arg Ser Asp Glu Ala Val Tyr Gly Lys Gly
    130                 135                 140
Val Lys Arg Ser Leu Pro Asp Glu Gln Thr Leu Ala Glu His Leu Val
145                 150                 155                 160
Arg Lys Ala Ala Ile Trp Ala Leu Glu Gln Pro Phe Met Asp Asp
                165                 170                 175
Leu Arg Asn Glu Gln Asp Gln Leu Leu Thr Lys Leu His Ala
            180                 185                 190
Leu Ala Ala Ile Leu Ala Glu Met Glu Phe Thr Gly Val Asn Val Asp
        195                 200                 205
Thr Lys Arg Leu Glu Gln Met Gly Ser Glu Leu Ala Glu Gln Leu Arg
    210                 215                 220
Ala Ile Glu Gln Arg Ile Tyr Glu Leu Ala Gly Gln Glu Phe Asn Ile
225                 230                 235                 240
Asn Ser Pro Lys Gln Leu Gly Val Ile Leu Phe Glu Lys Leu Gln Leu
                245                 250                 255
Pro Val Leu Lys Lys Thr Lys Thr Gly Tyr Ser Thr Ser Ala Asp Val
            260                 265                 270
Leu Glu Lys Leu Ala Pro His His Glu Ile Val Glu Asn Ile Leu His
        275                 280                 285
Tyr Arg Gln Leu Gly Lys Leu Gln Ser Thr Tyr Ile Glu Gly Leu Leu
    290                 295                 300
Lys Val Val Arg Pro Asp Thr Gly Lys Val His Thr Met Phe Asn Gln
305                 310                 315                 320
Ala Leu Thr Gln Thr Gly Arg Leu Ser Ser Ala Glu Pro Asn Leu Gln
                325                 330                 335
Asn Ile Pro Ile Arg Thr Pro Leu Gly Arg Lys Ile Arg Gln Ala Phe
            340                 345                 350
Val Pro Ser Glu Pro Asp Trp Leu Ile Phe Ala Ala Asp Tyr Ser Gln
        355                 360                 365
Ile Glu Leu Arg Val Leu Ala His Ile Ala Asp Asp Asn Leu Ile
    370                 375                 380
Glu Ala Phe Gln Arg Asp Leu Asp Ile His Thr Lys Thr Ala Met Asp
```

-continued

```
            385                 390                 395                 400
        Ile Phe Gln Leu Ser Glu Glu Val Thr Ala Asn Met Arg Arg Gln
                        405                 410                 415
        Ala Lys Ala Val Asn Tyr Gly Ile Val Tyr Gly Ile Ser Asp Tyr Gly
                    420                 425                 430
        Leu Ala Gln Asn Leu Asn Ile Thr Arg Lys Glu Ala Glu Phe Ile
                    435                 440                 445
        Glu Arg Tyr Phe Ala Ser Phe Pro Gly Val Lys Gln Tyr Met Glu Asn
                450                 455                 460
        Ile Val Gln Glu Ala Lys Gln Lys Gly Tyr Val Thr Thr Leu Leu His
        465                 470                 475                 480
        Arg Arg Arg Tyr Leu Pro Asp Ile Thr Ser Arg Asn Phe Asn Val Arg
                        485                 490                 495
        Ser Phe Ala Glu Arg Thr Ala Met Asn Thr Pro Ile Gln Gly Ser Ala
                    500                 505                 510
        Ala Asp Ile Ile Lys Lys Ala Met Ile Asp Leu Ala Ala Arg Leu Lys
                    515                 520                 525
        Glu Glu Gln Leu Gln Ala Arg Leu Leu Leu Gln Val His Asp Glu Leu
                    530                 535                 540
        Ile Leu Glu Ala Pro Lys Glu Gly Ile Glu Arg Leu Cys Glu Leu Val
        545                 550                 555                 560
        Pro Glu Val Met Glu Gln Ala Val Thr Leu Arg Val Pro Leu Lys Val
                        565                 570                 575
        Asp Tyr His Tyr Gly Pro Thr Trp Tyr Asp Ala Lys
                    580                 585
```

<210> SEQ ID NO 5
<211> LENGTH: 17
<212> TYPE: DNA
<213> ORGANISM: Bacillus stearothermophilus

<400> SEQUENCE: 5
cattttgctg ccggtca                                              17

<210> SEQ ID NO 6
<211> LENGTH: 20
<212> TYPE: DNA
<213> ORGANISM: Bacillus stearothermophilus

<400> SEQUENCE: 6
gtaaaacgac ggccagtctt                                           20

<210> SEQ ID NO 7
<211> LENGTH: 20
<212> TYPE: DNA
<213> ORGANISM: Bacillus stearothermophilus

<400> SEQUENCE: 7
gtaaaacgac ggccagtcgg                                           20

<210> SEQ ID NO 8
<211> LENGTH: 20
<212> TYPE: DNA
<213> ORGANISM: Bacillus stearothermophilus

<400> SEQUENCE: 8
cattttgctg ccggtcagaa                                           20

<210> SEQ ID NO 9
<211> LENGTH: 26
<212> TYPE: DNA
<213> ORGANISM: Bacillus stearothermophilus

<400> SEQUENCE: 9
gccgttaact acggtatcgt ttacgg                                    26

<210> SEQ ID NO 10
<211> LENGTH: 36

```
-continued

<212> TYPE: DNA
<213> ORGANISM: Bacillus stearothermophilus

<400> SEQUENCE: 10
cattccgatt cggaccccac tggggcggaa aatccg                        36

<210> SEQ ID NO 11
<211> LENGTH: 24
<212> TYPE: DNA
<213> ORGANISM: Bacillus stearothermophilus

<400> SEQUENCE: 11
sssssstgta aaacgacggc cagt                                     24
```